US010591392B2

(12) United States Patent
Torres et al.

(10) Patent No.: US 10,591,392 B2
(45) Date of Patent: *Mar. 17, 2020

(54) SIMULTANEOUS DEHYDRATION AND STAINING OF TISSUE FOR DEEP IMAGING

(71) Applicant: APPLIKATE TECHNOLOGIES LLC, Weston, CT (US)

(72) Inventors: Richard Torres, East Haven, CT (US); Michael Levene, New Haven, CT (US)

(73) Assignee: APPLIKATE TECHNOLOGIES LLC, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,019

(22) Filed: Jul. 3, 2014

(65) Prior Publication Data

US 2016/0003715 A1 Jan. 7, 2016

(51) Int. Cl.
*G01N 1/30* (2006.01)
*G01N 33/483* (2006.01)

(52) U.S. Cl.
CPC .......... *G01N 1/30* (2013.01); *G01N 33/4833* (2013.01)

(58) Field of Classification Search
CPC .......... C12Q 2563/107; C12Q 1/6816; C12Q 2563/173; Y10S 436/80; G01N 1/30; G01N 33/4833; G01N 2001/302; G01N 2001/305; G01N 21/6428; G01N 21/6458; G01N 33/542; G01N 33/573; G01N 33/58; G01N 2021/6439
See application file for complete search history.

(56) References Cited

U.S. PATENT DOCUMENTS

| | | | |
|---|---|---|---|
| 6,232,092 B1 | 5/2001 | Rogers | |
| 6,922,279 B2 | 7/2005 | Sun et al. | |
| 7,666,620 B2 | 2/2010 | Wiederhold | |
| 8,216,808 B2 | 7/2012 | Donndelinger | |
| 8,221,996 B2 | 7/2012 | Morales et al. | |
| 8,323,273 B2 | 12/2012 | Rylander et al. | |
| 8,445,284 B2 | 5/2013 | Lapen et al. | |
| 8,467,493 B2 | 6/2013 | Purchio et al. | |
| 2009/0226059 A1 | 9/2009 | Levenson et al. | |
| 2010/0144002 A1 | 6/2010 | Donndelinger | |
| 2010/0173295 A1* | 7/2010 | Lenz | G01N 1/30 435/6.11 |
| 2010/0323395 A1 | 10/2010 | Ulbrich et al. | |
| 2012/0081518 A1 | 4/2012 | Liu et al. | |
| 2012/0196320 A1 | 8/2012 | Seibel et al. | |
| 2012/0276583 A1 | 11/2012 | Visinoni et al. | |
| 2012/0321159 A1 | 12/2012 | Keller et al. | |
| 2012/0322099 A1* | 12/2012 | Lapen | G01N 1/30 435/40.5 |
| 2013/0023008 A1 | 1/2013 | Becker et al. | |
| 2013/0052637 A1 | 2/2013 | Kovar et al. | |
| 2013/0178916 A1 | 7/2013 | Rylander et al. | |

FOREIGN PATENT DOCUMENTS

| | | |
|---|---|---|
| CN | 101181152 | 5/2010 |
| EP | 1676117 | 9/2009 |
| EP | 2 506 009 | 10/2012 |
| WO | 2001085028 | 11/2001 |
| WO | 2003060477 | 7/2003 |
| WO | 2004010118 | 1/2004 |
| WO | 2013071003 | 5/2013 |

OTHER PUBLICATIONS

Mohun et al. Embedding embryos for high-resolution episcopic microscopy (HREM). Cold Spring Harb Protoc. 2012;6:678-80.*
Rolls G. Fixation and Fixatives. Leica Biosystems. 2012;1-14.*
Tarnowski et al. DAPI as a useful stain for nuclear quantitation. Biotech Histochem. 1991;66(6):297-302.*
Zucker et al. Confocal laser scanning microscopy of morphology and apoptosis in organogenesis-stage mouse embryos. Methods Mol. Biol. 2000;135:191-202.*
Saponin. Zoospores and saponins. Zoospores and saponins. 2013;1-5.*
Torres et al. High-Resolution, 2- and 3-Dimensional Imaging of Uncut, Unembedded Tissue Biopsy Samples. Arch Pathol Lab Med. 2014;138:395-402.*
Parra et al., "Multiphoton microscopy of cleared mouse organs." 2010, J. Biomed. Opt. 15:036017.
Vesuna et al., "Multiphoton fluorescence, second harmonic generation, and fluorescence lifetime imaging of whole cleared mouse organs." 2011, J. Biomed. Opt. 16:106009.
Fu et al., "Microtome-Free 3-Dimensional Confocal Imaging Method for Visualization of Mouse Intestine With Subcellular-Level Resolution." 2009, Gastroenterology 137:453-465.
Dechet et al., "Prospective Analysis of Computerized Tomography and Needle Biopsy With Permanent Sectioning to Determine the Nature of Solid Renal Masses in Adults." 2003, J. Urol. 169:71-74.
Bewersdorf et al., "Multifocal multiphoton microscopy." 1998, Opt. Letters 23:655-657.
Oron et al., "Scanningless depth-resolved microscopy." 2005, Opt. Express 13:1468-1476.
Zhu et al. "Simultaneous spatial and temporal focusing of femtosecond pulses." 2005, Opt. Express 13:2153-2159.

(Continued)

*Primary Examiner* — Lynn Y Fan
(74) *Attorney, Agent, or Firm* — Brown Rudnick LLP; Thomas C. Meyers

(57) ABSTRACT

A biopsy-sized tissue sample is stained for quick imaging. A significant amount of permeation enhancer is included in a mixed solution of permeant enhancer, fixative or dehydrant, and one or two fluorescent dyes to simultaneously dehydrate and dye the tissue sample. The permeation enhancer, e.g., 10% to 50% in the mixed solution, achieves an image of dyed tissue in the contacted tissue sample at a depth of at least 200 um within no more than 1.5 hours. One of the fluorescent dyes is a fluorescent nuclear dye such as DAPI, SYTOX green, acridine orange, propidium iodide, or a Hoechst dye. The other fluorescent dye is a fluorescent protein dye such as eosin or rhodamine B. The tissue sample is cleared with a clearing agent having a refractive index of at least 1.4[R2], e.g., using BABB. The mixed solution may further include Chloroform or other morphology preservative.

7 Claims, 15 Drawing Sheets

(56) References Cited

OTHER PUBLICATIONS

Zysk et al., "Optical coherence tomography: a review of clinical development from bench to bedside." 2007, J. Biomed. Opt. 12:051403.
Bizheva et al., "Imaging ex vivo healthy and pathological human brain tissue with ultra-high-resolution optical coherence tomography." 2005, J. Biomed. Opt. 10:011006.
Ragan et al., "High-resolution whole organ imaging using two-photon tissue cytometry." 2007, J. Biomed. Opt. 12:014015.
Dechet et al., "Prospective Analysis of Intraoperative Frozen Needle Biopsy of Solid Renal Masses in Adults." 1999, J. Urol. 162:1282-1284.
Zehbe et al., "Going beyond histology. Synchrotron micro-computed tomography as a methodology for biological tissue characterization: from tissue morphology to individual cells." 2010, J. R. Soc. Interface 7:49-59.
Ritman. "Current Status of Developments and Applications of Micro-CT." 2011, Annu. Rev. Biomed. Eng. 13:531-552.
Amir et al., "Simultaneous imaging of multiple focal planes using a two-photon scanning microscope." 2007, Opt. Letters 32:1731-1733.
International Search Report (ISR) dated Nov. 13, 2015 in International Application No. PCT/US2015/039079.
Rene J. Buesa, "Microwave-assisted tissue processing: real impact on the histology workflow", Annals of Diagnostic Pathology, 11, pp. 206-211, 2007.
Rene J. Buesa, "Productivity standards for histology laboratories", Annals of Diagnostic Pathology, 14, pp. 107-124, 2010.
Amount C. Ruifrok et al., "Quantification of Histochenical Staining by Color Deconvolution", Analytical and Quantitative Cytology and Histology, pp. 291-299.
Extended European Search Report dated Jan. 31, 2018 for European Patent Application No. 15814034.3 (6 Pages).

* cited by examiner

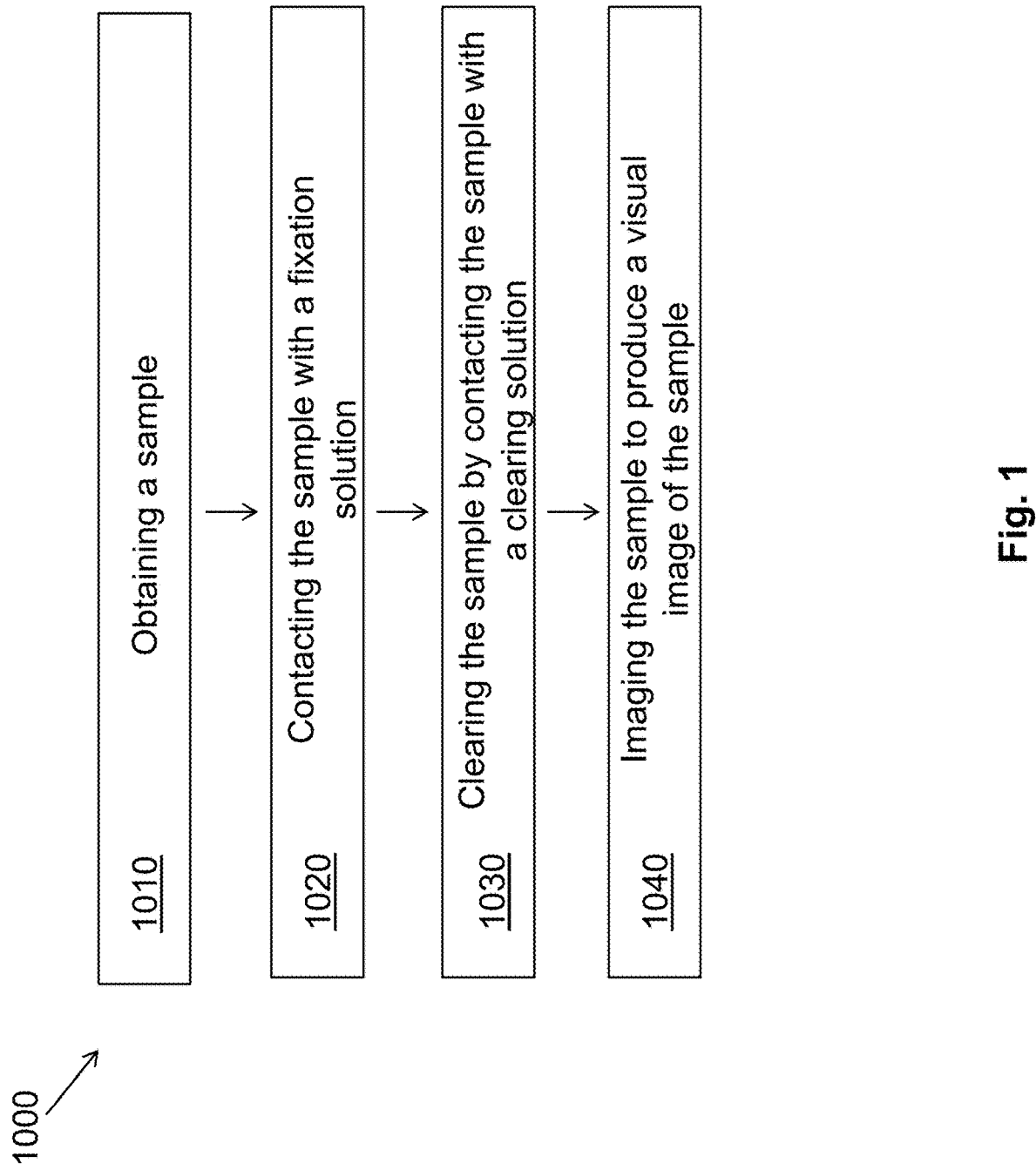

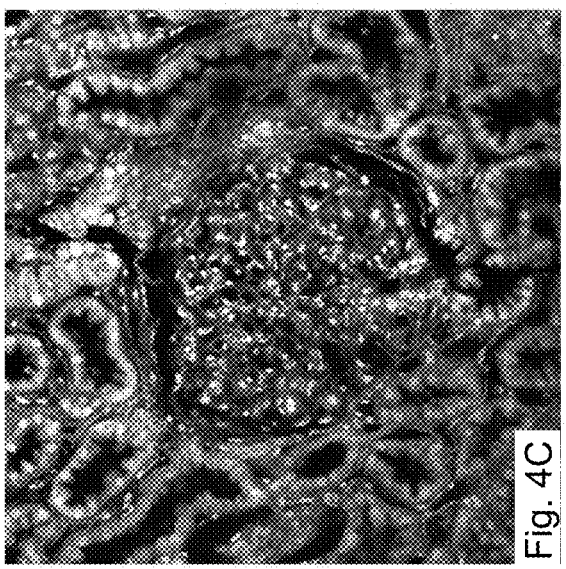
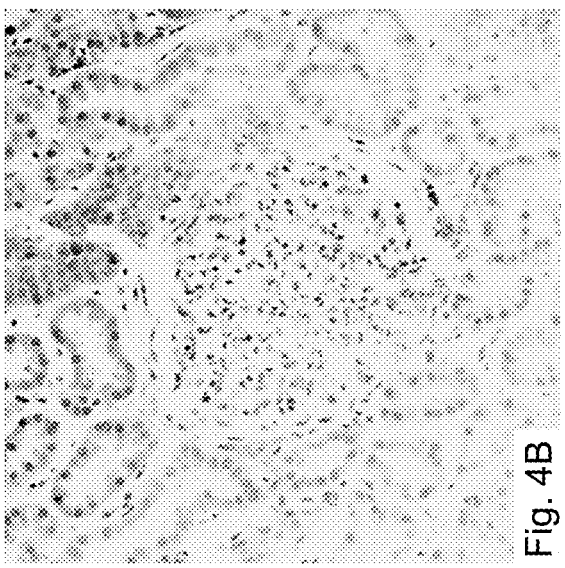
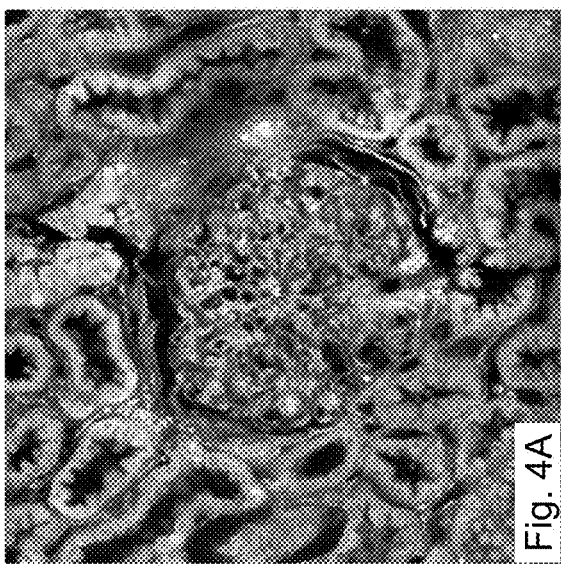
Fig. 4A – 4D

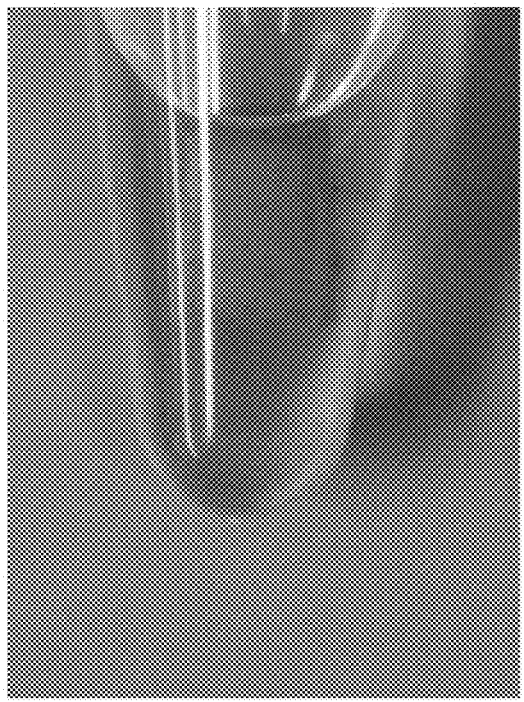
Fig. 9B
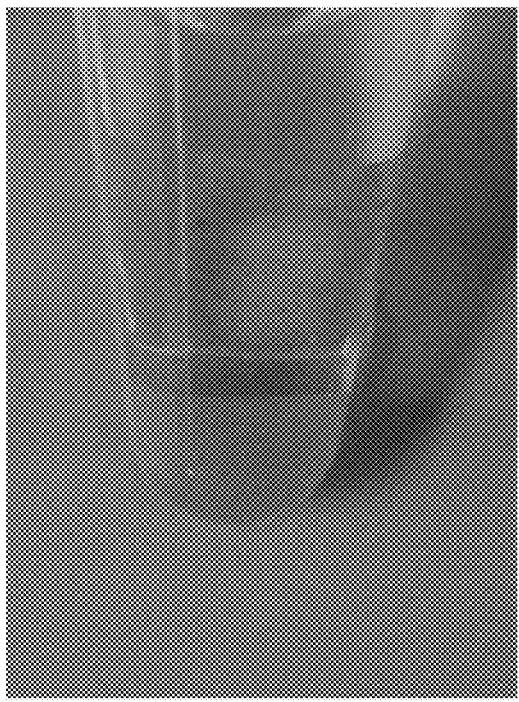
Fig. 9C
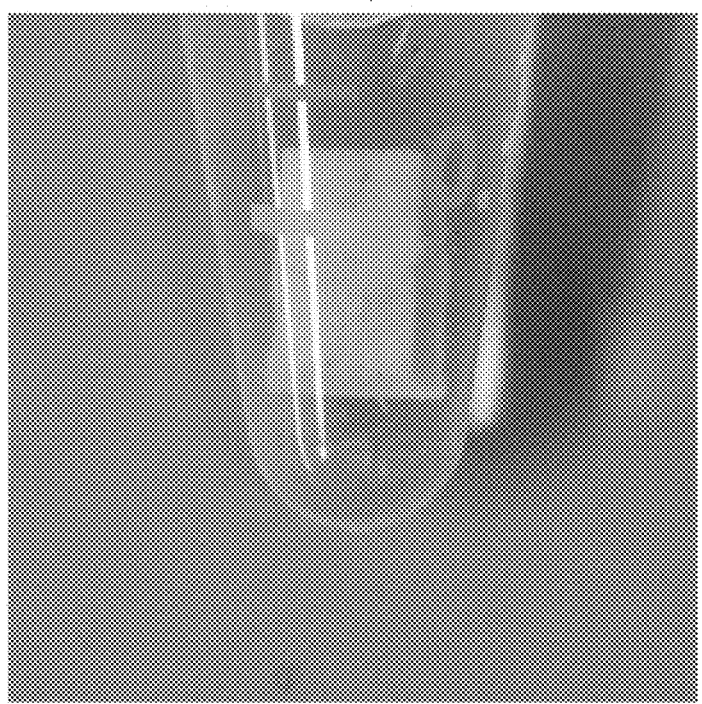
Fig. 9A
Fig. 9A – 9C

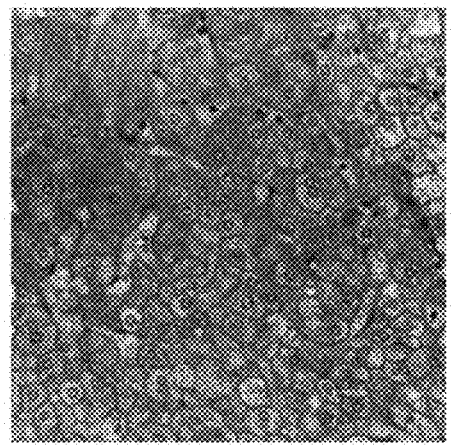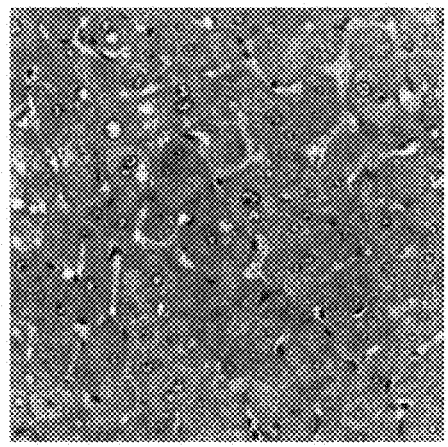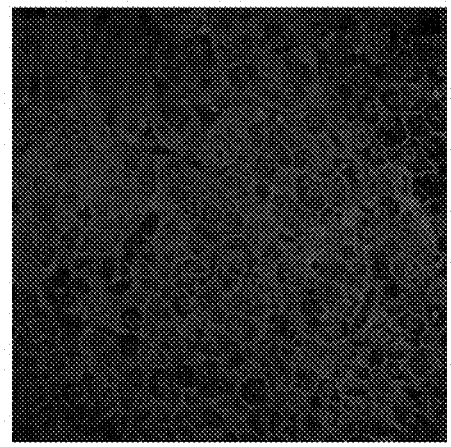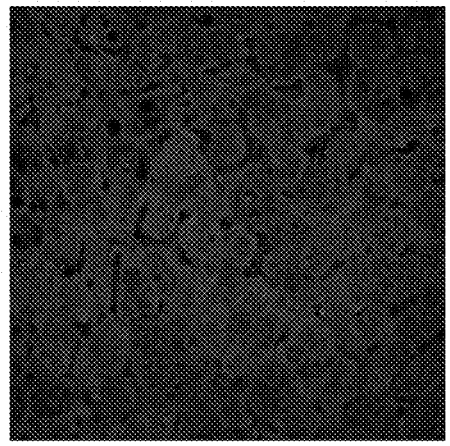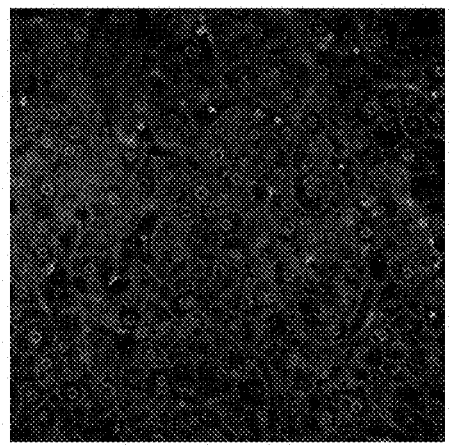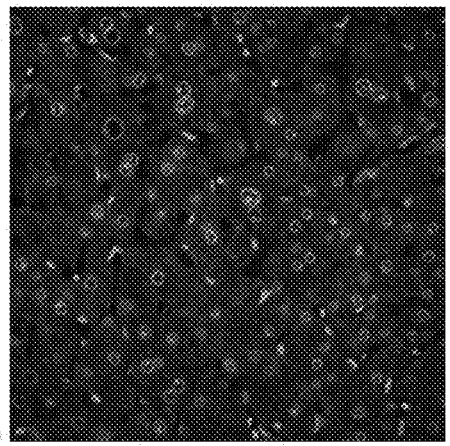
Fig. 11A – 11B
Fig. 11A
Fig. 11B

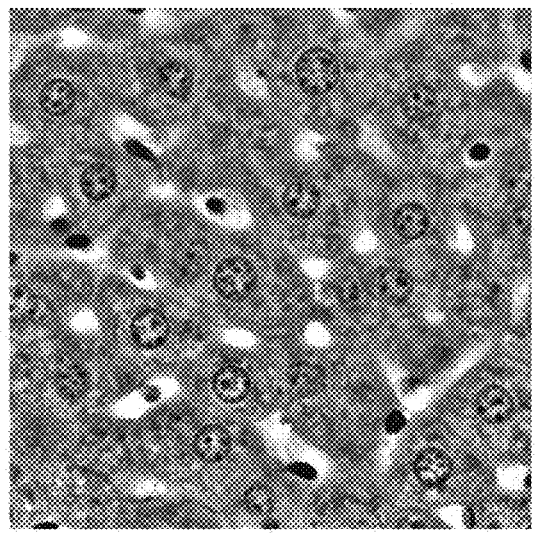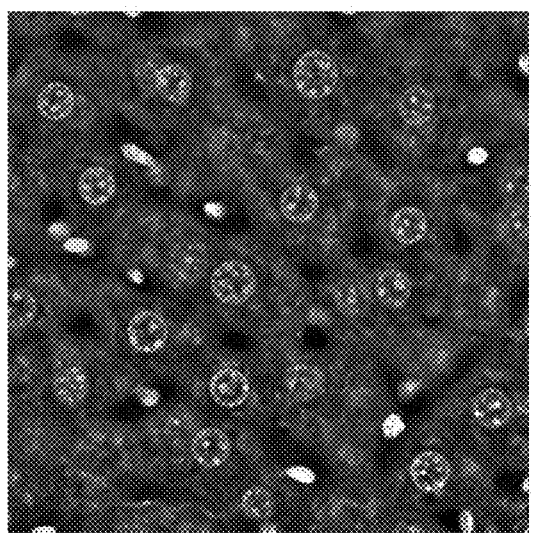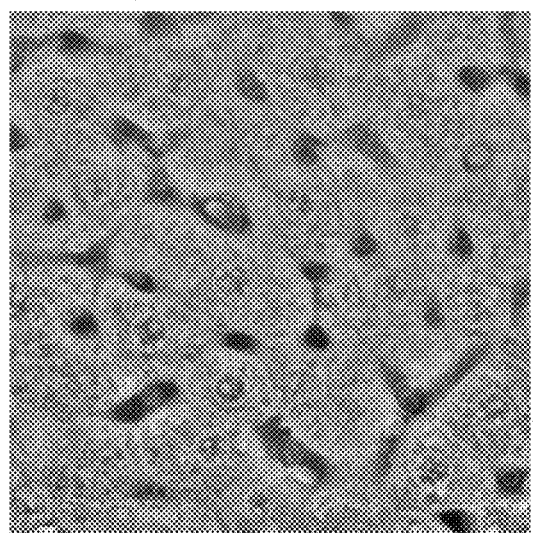
Fig. 14A
Fig. 14B
Fig. 14C
Inversion of logarithmic matrix conversion
Fig. 14A – 14C

006
SIMULTANEOUS DEHYDRATION AND STAINING OF TISSUE FOR DEEP IMAGING

STATEMENT REGARDING FEDERALLY SPONSORED RESEARCH OR DEVELOPMENT

This invention was made with government support under grant No. DBI-0953902 awarded by the National Science Foundation. The government has certain rights in the invention.

BACKGROUND OF THE INVENTION

Automated histology laboratory instrumentation has significantly improved the ability of pathology laboratories to process tissue samples, particularly biopsy samples, in a relatively rapid and consistent manner. These efforts have also reduced somewhat the dependence on skilled histology personnel and improved the quality of diagnostic material. Similarly, with all its limitations, the current evolution of slide-scanning technology has begun to make remote viewing and digital storage of tissue samples a reality. But there are aspects of traditional paraffin-embedded, microtome-cut, hematoxylin-eosin (H&E)-stained slices for routine pathologic evaluation that limit the ability to make more significant advances in the speed, quality, and completeness of tissue biopsy evaluation.

Visual examination of tissue samples remains a mainstay of diagnostic analysis of tissue but there is an increasing role of ancillary studies such as that derived from genetic and proteomic data. This trend is dependent on the availability of sufficient and adequately preserved tissue which competes with the interest for smaller samples and faster results. In addition, incomplete sample evaluation, artifacts of preparation, non-quantitative interpretation, limited growth pattern information, and an extended manual preparative process are some of the aspects of traditional slide-based histologic analysis of human samples that limit advancements in pathology. These are particularly relevant for the usual initial diagnostic step in pathologic assessment which is often core biopsies or fine needle aspirations.

Many alternative tissue processing and imaging approaches have been proposed to address limitations of traditional processing techniques. More recent ones include high-resolution x-ray computed tomography (Zehbe et al., 2010, J. R. Soc. Interface 7:49-59; Ritman, 2011, Annu. Rev. Biomed. Eng. 13:531-552) and optical coherence tomography (Zysk et al., 2007, J. Biomed. Opt. 12:051403-051403-21; Bizheva et al., 2005, J. Biomed. Opt. 10:11006-11006-07). These approaches have the advantages of being applicable to unprocessed fresh tissue and allowing complete 3-dimensional visual examination while leaving tissue unaltered and amenable to further characterization. At the present time, neither technique is able to produce images of sufficient resolution and contrast for adequate routine pathology evaluation.

Multiphoton microscopy (MPM), on the other hand, has the ability to provide images with excellent cellular detail and is a popular, powerful method for analysis of research samples. Use of short-pulse laser light also permits concurrent mapping of second-harmonic generation (SHG), making it possible to simultaneously produce quantifiable images of repeating asymmetric protein structures such as collagen and amyloid. Unfortunately, although the long wavelengths used in MPM can image deeper into tissue than confocal microscopy, traditional methods can only achieve clear images at depths of at most 50 µm with formalin-fixed specimens. Previous attempts to use MPM for imaging through fixed tissue have used serial sectioning (Ragan et al., 2007, J. Biomed. Opt. 12:014015-014015-9) or serial tissue ablation (Dechet et al., 1999, J. Urol. 162:1282-1284), both of which result in the destruction of the tissue specimen during the course of imaging, making them nonviable for routine clinical use.

The above noted points indicate that novel methods of tissue processing for imaging of uncut and un-embedded samples are desirable. Tissue clearing presents a useful approach to practically and significantly increase the accessible depth of imaging for various modes of optical sectioning microscopy. Past efforts to obtain high resolution images at depth with clearing have been limited to a small set of applications. These past approaches have failed to develop a processing method that can achieve the speed necessary for adequate implementation in routine pathology and many types of investigative work. They have also not been able to faithfully reproduce the types of coloration that trained specialists in morphologic evaluation are accustomed to interpreting.

Thus, there remains a need for a practical new processing method that can obtain high resolution images of tissue at depth in a relatively short period of time. Additionally, there is a need for these depth images to be obtained in a manner that makes them instantly recognizable by pathologists and microanatomy investigators. The present invention addresses this unmet need.

BRIEF SUMMARY OF THE INVENTION

A method of processing a tissue sample is described. The method includes the steps of obtaining a tissue sample, and contacting the tissue sample with a fixative solution comprising at least one fixative and at least one fluorescent dye. In one embodiment, the method further includes the step of contacting the tissue sample with a clearing solution. In another embodiment, the method further includes the step of imaging the tissue sample to produce a visual image of the tissue sample. In another embodiment, the at least one fluorescent dye is selected from the group consisting of eosin, DAPI, SYTOX green, acridine orange, rhodamine B, propidium iodide, and a Hoechst dye. In another embodiment, the at least one fixative is methacarn. In another embodiment, the fixative solution further comprises a permeation enhancer. In another embodiment, the step of contacting the tissue sample with a fixative solution is performed at about 45° C. In another embodiment, the fixative solution further comprises a red blood cell lysing agent. In another embodiment, the step of contacting the tissue sample with a fixative solution is performed over a period of time of about 1 hour. In another embodiment, the clearing solution is comprised of benzyl alcohol and benzyl benzoate. In another embodiment, the ratio of benzyl alcohol to benzyl benzoate is about 1:2. In another embodiment, the step of contacting the tissue sample with a clearing solution is performed over a period of time of about 30 minutes. In another embodiment, the steps of contacting the tissue sample with a fixative solution and contacting the tissue sample with a clearing solution are performed over a period of time of about 1.5 hours. In another embodiment, the tissue sample is fixed prior to obtaining the tissue sample.

Also described is a method of imaging a tissue sample. The method includes the steps of obtaining a tissue sample, contacting the tissue sample with a fixative solution comprising at least one fluorescent dye, contacting the tissue sample with a clearing solution, and producing a tissue sample image by measuring intensity values of the fluorescence of the tissue sample, and converting the intensity values to effective optical densities, such that the optical densities recreate the coloration of a stain in a produced image of the tissue sample. In one embodiment, the tissue sample image is produced using multiphoton microscopy (MPM). In another embodiment, the step of producing a tissue sample image further comprises second harmonic generation (SHG). In another embodiment, the sample image is a three dimensional (3-D) sample image. In another embodiment, the sample image is obtained at a sample depth of greater than 200 µm. In another embodiment, the intensity values are converted to effective optical densities using an exponential pseudo-coloration process.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

The patent or application file contains at least one drawing executed in color. Copies of this patent or patent application publication with color drawing(s) will be provided by the Office upon request and payment of the necessary fee.

FIG. 1 depicts a flow chart illustrating an exemplary method for processing and imaging a sample.

FIG. 2, comprising

FIG. 3, comprising FIG. 3A is an image of a prostate tissue sample acquired at medium power. FIG. 3B is an image of a liver tissue sample acquired at high power. FIG. 3C is an image of a breast tissue sample acquired at medium power. FIG. 3D is an image of a kidney tissue sample acquired at medium power. Images are from depths ranging from 200 to 500 µm. Morphologic detail was comparable at 1 mm in depth.

FIG. 4, comprising FIGS. 4A-4C, depicts multichannel data for a kidney section. FIG. 4A is an image of intrinsic fluorescence dominated by signal from cell cytoplasm. FIG. 4B is an image of inverted nucleic acid fluorescence channel highlighting predominantly nuclear DNA and some cytoplasmic RNA. FIG. 4C is an image of combined intrinsic fluorescence and nuclear fluorescence (gray scale) with second-harmonic generation channel in red showing distribution of collagen fibers around a normal glomerulus.

FIG. 6, comprising

FIG. 7, comprising FIG. 7A is an image depicting cytokeratin (CK) 7 stain of normal kidney showing expected pattern of transition to positive staining on descending medullary cords. FIG. 7B is an image depicting appropriate lack of staining of same renal tissue with CK20 (original magnifications ×4 [FIGS. 5A and 5B]).

FIG. 8, comprising FIG. 8A is an image depicting approximately 1-mm cubic section of normal human liver obtained by multiphoton microscopy on cleared tissue without staining (intrinsic fluorescence only, low power). FIG. 8B is an image depicting similar sized block of normal human breast tissue, which has been fixed, cleared, and stained with the nucleic acid dye SYTOX Green (low power). FIG. 8C is a perspective image of 3-D reconstruction of collagen from normal human kidney (approximately 200×200×40 µm).

FIG. 9, comprising FIGS. 9A-9C, depicts various tissue samples. FIG. 9A is an image of an uncleared sample. FIG. 9B is an image of a sample produced with a traditional method of tissue clearing involving increasing gradients of ethanol (50%, 75%, 100%), followed by immersion in hexane, followed by immersion in benzyl alcohol:benzyl benzoate in a 1:2 ratio, executed in a time period of 1.25 hours. FIG. 9C is an image depicting a sample processed using the methods of the present invention over the same period of 1.25 hours. At time 1.25 hours (15 mins clearing post processing), clearing with the method of the present invention shows deeper clearing (smaller core of uncleared volume) compared to traditional processing. The traditional method also shows leeching of fluorescent dye into BABB (red tint to liquid).

FIG. 11, comprising FIGS. 11A-11B, depicts images of tissues processed using traditional processing methods and methods of the present invention. FIG. 11A is a series of images of tissues processed using traditional processing methods. FIG. 11B is a series of images of tissues processed using the methods of the present invention. The methods of the present invention result in better separation of nuclear and protein fluorescence signals with inexpensive dye combinations and exhibit improved detail at 500 µm deep with significantly less cell shrinkage.

FIG. 14, comprising FIGS. 14A-14C, depicts images of tissues processed using pseudo-H&E. FIG. 14A is an image of tissue processed with nuclear stain. FIG. 14B is an image of tissue processed with protein fluorescence. FIG. 14C is an image of tissue imaged with an inversion of logarithmic matrix conversion using images depicted in FIGS. 14A and 14B.

DETAILED DESCRIPTION

Figures 2A, 2B, 2C, 2D:
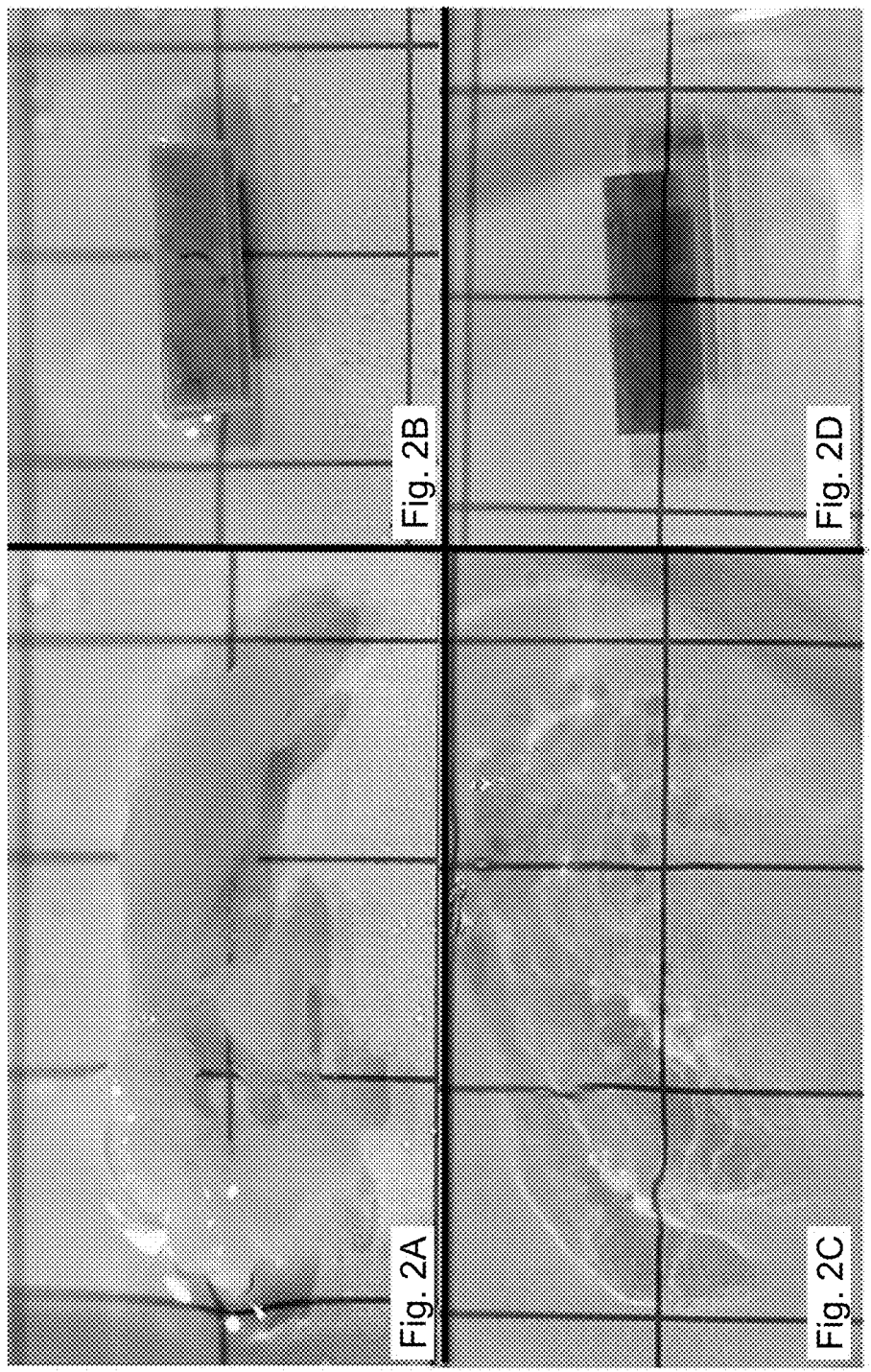
FIGS. 2A-2D, depicts images of examples of clearing. Formalin-fixed tissue sections of breast (FIG. 2A) and liver (FIG. 2B) before and after (FIG. 2C and FIG. 2D, respectively) a benzyl alcohol/benzyl benzoate clearing protocol. Note near-complete transparency of breast tissue specimen and translucency of liver specimen with some remaining pigment. Grid line spacing is 0.9 cm.
Figure 3A:
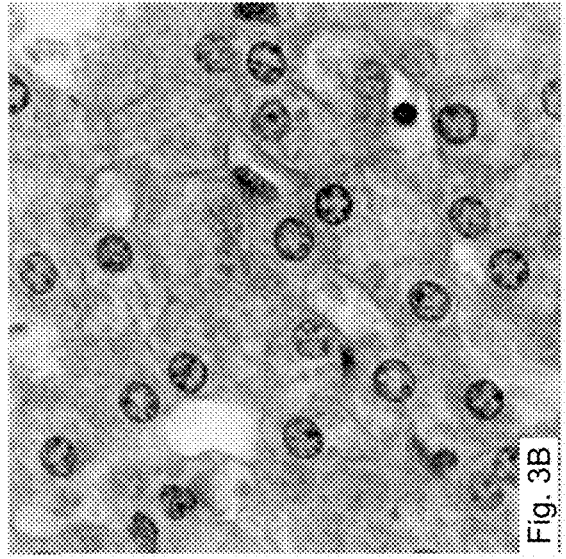
FIGS. 3A-3D, depicts multiphoton microscopy images of clarified normal human tissue. Specimens were stained either with SYTOX Green or acridine orange nucleic acid dyes during dehydration steps.
Figure 3B:
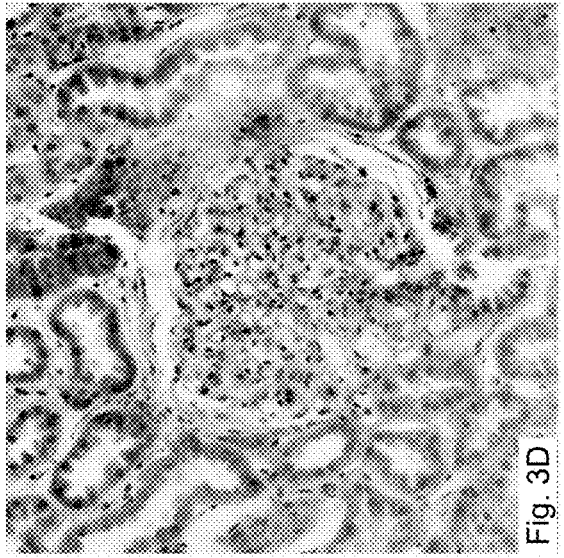
Figure 3C:
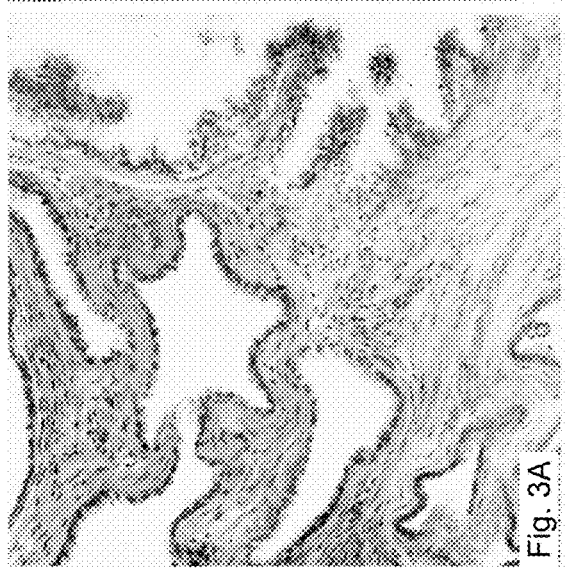
Figure 3D:
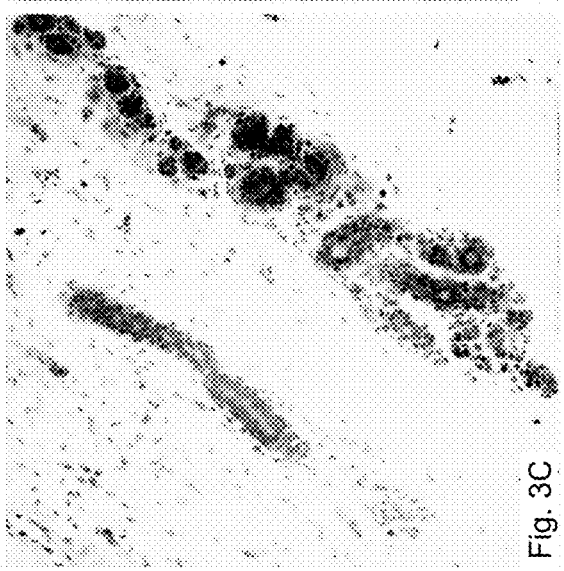

It is to be understood that the figures and descriptions of the present invention have been simplified to illustrate elements that are relevant for a clear understanding of the present invention, while eliminating, for the purpose of clarity, many other elements found in the art related to histology, tissue processing, and the like. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Although any methods, materials and components similar or equivalent to those described herein can be used in the practice or testing of the present invention, the preferred methods and materials are described.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" and "approximately" as used herein when referring to a measurable value such as an amount, a temporal duration, and the like, are meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "fixation" refers any process which halts cellular degradation such as by arresting enzymatic function through protein crosslinking or dehydration.

As used herein, the term "dehydration" refers to removal of water from the sample to aid in preparation for imaging by such effects as arresting enzymatic function and/or creating a solvent environment that is at least partially miscible with a hydrophobic fluid.

As used herein, the term "BABB" refers to a solution of benzyl alcohol and benzyl benzoate. For example, BABB may refer to a solution of benzyl alcohol and benzyl benzoate, wherein the ratio of benzyl alcohol to benzyl benzoate is about 1:2.

As used herein, the term "tissue" means any structure derived from an organism. The term also encompasses any structure excised or removed from an organism. As used herein, an organism from which "tissue" is derived need not be exclusively a human being, but rather the term encompasses tissue derived from any organism. With respect to humans, the term includes a structure derived from either a living human or a cadaver. In certain embodiments, tissue is derived from a mammal, including, but not limited to, humans, rats, mice and sheep.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to methods of tissue preparation and image-analysis that allow for the practical implementation of the deep imaging of tissue specimens. The methods described herein reduce the number of steps for tissue processing, decrease the time required to process tissues, and improve the clarity and contrast in samples, thereby permitting deep tissue imaging of the sample. As demonstrated herein, the methods of the present invention provide complete visualization of biopsy-sized specimens without the need for the time-consuming and manually intensive post-clearing steps, thereby reducing the time between biopsy through morphologic assessment. In non-limiting examples, cleared biopsy specimens can be provided to pathologists for direct visualization or scanned for image distribution. In another non-limiting example, a primary diagnosis may be rendered based on the images, with subsequent studies ordered if necessary.

In part, the present invention provides a method for image analysis that allows reproduction of images essentially indistinguishable from traditional histology stains. This method provides images of samples that mimic common pathology stains, resulting in the accurate and efficient interpretation of the images. Contrary to currently used color separation algorithms, the methods described herein invert these color separation techniques using the fluorescence of the sample, whether inherent or resulting from a fluorescent dye, to faithfully recreate images comprising the expected colorization of tissues resulting from common stains such as hematoxylin/eosin and wright/giemsa, allowing the images to be easily interpreted by pathologists. Contrary to past efforts of pseudo-colorization, the methods described herein use exponential conversion equations, more closely matching the optical qualities of fluorescence emission to those of light absorption with traditional illumination of thin sections. As demonstrated herein, the methods of the present invention result in the production of images that have resolution and fields of view similar to those produced using current histological methods, provide a contrast similar to that obtained with commonly used histologic stains, and permit subsequent traditional processing without apparent adverse effects. The multichannel method described herein provides straightforward pseudocolorization that represents morphology in an analogous method to traditional stains, allowing pathologists to easily recognize salient histologic features.

With biopsies, there is often a trade-off between keeping sufficient tissue for additional stains or molecular analysis and adequate hematoxylin and eosin (H&E) histology. The necessarily sparse sampling of traditional physical wax-embedding and cutting histology techniques can miss important features. For example, colonic polyps may be missed, small foci of prostate cancer may be non-diagnostic, and focal renal lesions may be unapparent. This problem is compounded by the need to discard initial block shavings for complete sections, particular in imperfectly embedded specimens. The methods described herein obviate these issues that occur when using current histological methods while permitting image reconstruction of entire or deep portions of biopsy specimens.

Methods

In one aspect, the present invention provides methods of processing and imaging a histological sample. In one embodiment, the method comprises the step of obtaining a sample. The sample can generally be any type of sample. For example, the sample can be a cell or group of cells, an organism, a tissue, cell lysates, a cell culture medium, a bioreactor sample, and so on. In a preferred example, the sample is a tissue sample. In another embodiment, the sample is a fluid sample in which the cellular component has been concentrated such as by centrifugation or filtering. Non-limiting examples of tissues include skin, muscle, bowel, breast, heart, kidney, lung, liver, skin, placenta, prostate, pancreas, uterus, bone, bone marrow, brain, stomach, muscle, cartilage, lymph node, adipose tissue, tonsil, gall bladder, and spleen, as well as the cellular component of cerebrospinal fluid, pleural fluid, ascites fluid, or synovial fluid. In one embodiment, the tissue is liver tissue. In another embodiment, the tissue is kidney tissue. In another embodiment, the tissue is breast tissue. In another embodiment, the tissue is prostate tissue. The sample may be obtained through any method known in the art, as would be understood by one skilled in the art. In some embodiments, the sample is obtained during surgery, biopsy, fine needle aspiration, culture, or autopsy. In one embodiment, the sample is a fresh sample. In another embodiment, the sample is a fixed sample. In one embodiment, the tissue sample is fixed prior to obtaining the tissue sample.

FIG. 1 depicts a flow chart illustrating an exemplary method 1000 for processing and imaging a sample. Method 1000 comprises obtaining a sample 1010, and contacting the sample 1020 with a fixation solution. In a preferred embodiment, the sample is a tissue sample. In certain embodiments, the fixation solution comprises at least one dehydrant and at least one fluorescent dye. In one embodiment, method 1000 comprises clearing the sample 1030 by contacting the sample with a clearing solution to provide increased depth and clarity for imaging the sample 1040. In one embodiment, the sample is fixed prior to being contacted with a solution comprising a fixative or dehydrant and at least one fluorescent dye. In another embodiment the fresh tissue is placed directly in a combination fixation/dehydration fluid with dye or dyes. In some embodiment, the step of imaging the sample is performed in combination with an additional imaging method, such as second harmonic generation (SHG). (FIG. 1).

In one aspect, the method of the present invention further comprises the step of dehydrating the sample. Dehydration facilitates the removal of water from a sample so that clearing agents with low water solubility can subsequently be used. It should be appreciated that a dehydrant or a dehydration solution may also be used as a fixative or for fixing a sample. As used herein, the term "dehydrant" refers to a water-miscible anhydrous fluid. Non-limiting examples of dehydrants include alcohols such as methanol, ethanol, and propanol. In one embodiment, the dehydrant is methacarn. In another embodiment, the dehydrant is methanol. In one embodiment, the dehydration step functions as a fixative and takes place without prior fixation of the sample. In other embodiments, the dehydration step is performed after fixation of the sample. In one embodiment, the dehydration step is performed after fixation of the sample using a fixation solution comprised of formalin.

The dehydration step can be performed for any suitable length of time. The length of time can generally be any length of time suitable for rendering the sample miscible with the clearing agent. The length of time can also generally be any length of time suitable for preserving the sample. In certain embodiments the period of time may be from about 1 minute, about 5 minutes, about 15 minutes, about 30 minutes, about 1 hour, about 2 hours, about 3 hours, about 4 hours, about 5 hours, about 6 hours, about 12 hours, or about 24 hours. In one embodiment, the dehydration step is performed over a period of time about 1 hour. In another embodiment the dehydration step is performed over about 12 to 16 hours.

In one aspect, method of the present invention comprises the step of fixing the sample. The tissue sample may be fixed using any method known in the art, as would be understood by one skilled in the art. In one embodiment, the sample is fixed by contacting the sample with a fixative. In another embodiment, the sample is fixed by contacting the sample with a fixation solution. In one embodiment, the fixation solution is comprised of at least one fixative. In one embodiment, the fixative is a dehydrant. In another embodiment, the fixation solution is a dehydrant. In another embodiment, the fixation solution comprises at least one fixative and at least one permeant. Non-limiting examples of fixatives include aldehydes (e.g., formaldehyde (paraformaldehyde, formalin), glutaraldehyde, acrolein (acrylic aldehyde), glyoxal (ethanedial, diformyl), malonaldehyde (malonic dialdehyde), diacetyl (2,3-butanedione), and polyaldehydes; alcohols (i.e., protein-denaturing agents; e.g., acetic acid, methanol, ethanol), polyvinyl alcohols, heavy metal oxidizing agents (i.e., metallic ions and complexes; e.g., osmium tetroxide, chromic acid); agents of unknown mechanism, such as chloro-s-triazides, cyanuric chloride, carbodiimides, diisocyanates, diimido esters, diethylpyrocarbonate (diethyl oxydiformate, ethoxyformic anhydride), picric acid, mercuric chloride (corrosive sublimate, bichloride of mercury), and other salts of mercury, and acetone. In one embodiment, a combination of fixatives is used. Such combinations give rise to commonly termed formulations known to those in the art, such as Carnoy's fixatives, methacarn, Wolman's solution, Rossman's fluid, Gendre's fluid, Bouin's fluid, Zenker's fluid, Helly's fluid, B5 fixative, Susa fluid, Elftman's fixative, Swank and Davenport's fixative, Lillie's alcoholic lead nitrate, and cetylpyridinium chloride (C.P.C.). Additives can include, but are not limited to, such entities as tannic acid, phenol, transition metal salts (zinc), lanthanum, lithium, potassium. In one embodiment, the fixative is methacarn. In another embodiment, the fixative is formalin. In another embodiment, the fixative is an alcohol. In another embodiment, the fixative is methanol. In another embodiment, the fixative is a polyvinyl alcohol. In another embodiment, the fixative is formaldehyde. In another embodiment, fixation of the sample occurs ex vivo.

In some embodiments, at least one fluorescent dye is added to the sample during the fixation step, resulting in simultaneous fixing and staining of the sample. In other embodiments, at least one fluorescent dye is added to the sample during the dehydration step, resulting in simultaneous dehydration and staining of the sample. The incorporation of a fluorescent dye obviates the need for post-processing staining, which is a time-consuming step of traditional sample preparation. The fluorescent dye may be added directly to the sample during the fixation step. For example, the fluorescent dye may be added to the fixation solution. In another embodiment, the fluorescent dye is added to the sample after completion of the fixation step. In one embodiment, the fixation solution comprises a fixative and a fluorescent dye. In another embodiment, the fixative solution comprises at least one dehydrant and at least one fluorescent dye. In one embodiment, the fluorescent dye is added directly to the sample during the dehydration step. In one embodiment, the method of processing a tissue sample comprises the steps of obtaining a tissue sample, and contacting the tissue sample with a fixative solution comprising at least one dehydrant and at least one fluorescent dye.

The skilled artisan will understand that the present invention contemplates the use of any fluorescent dye that is compatible with the fixation step. Examples of fluorescent dyes include, but are not limited to, POPO-1, TOTO-3, TAMRA, BOXTO, BEBO, SYBR DX, SYTOX dyes, SYTO dyes, Alexa dyes, fluorescein, rhodamine, propidium idodide, Hoechst dyes, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo)benzoic acid (DABCYL), 5-(2'-aminoethyl)aminonaphthalene-1-sulfonic acid (EDANS), 8-Anilino-1-naphthalenesulfonic acid ammonium salt (ANS), 4-acetamido-4'-isothiocyanatostilbene-2,2' disulfonic acid, acridine, acridine isothiocyanate, acridine orange (N,N,N', N'-tetramethylacridine-3,6-diamine), R-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 2-(4-amidinophenyl)-1H-indole-6-carboxamidine (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl)aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron®Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, thiazole orange, riboflavin, rosolic acid, and terbium chelate derivatives. In one embodiment, the fluorescent dye is eosin. In another embodiment, the fluorescent dye is DAPI. In another embodiment, the fluorescent dye is SYTOX green. In another embodiment, the fluorescent dye is acridine orange. In another embodiment, the fluorescent dye is rhodamine B. In another embodiment, the fluorescent dye is a SYTO dye. In another embodiment, the fluorescent dye is propidium iodide. In another embodiment, the fluorescent dye is a Hoechst dye.

In certain embodiments, the fluorescent dye can selectively stain a particular organelle or component of a cell. In one embodiment, the fluorescent dye is a nuclear dye. Non-limiting examples of nuclear dyes include DAPI, SYTOX dyes, SYTO dyes, propidium iodide, acridine orange, and Hoechst dyes. In one embodiment, the nuclear dye is DAPI. In another embodiment, the fluorescent dye is a protein dye. Examples of protein dyes include, but are not limited to, eosin, Rhodamine B (RhB), and ANS. In another embodiment, intrinsic fluorescence of the cell is used to image the cellular protein. In another embodiment, the fluorescence is generated from a combination of at least one nuclear dye and at least one protein dye. In another embodiment, the fluorescence is generated from a nuclear dye and intrinsic fluorescence. In one embodiment, the at least one protein dye is eosin.

In certain embodiments, a morphology preservative is added to the sample during the fixation step and/or the dehydration step. The morphology preservative enhances maintenance of the nuclear structure of the cells, in that it maintains cell membranes intact for subsequent cytological staining and/or reduces shrinking or swelling during fixation or dehydration. Any morphology preservative that is compatible with the fixation step may be used in the invention, as would be understood by one of ordinary skill in the art. In a preferred embodiment, the morphology preservative is chloroform. The morphology preservative may be added directly to the sample during the fixation step. Alternatively, the morphology preservative may be added to the fixation solution. In one embodiment, the fixation solution is comprised of about 0% to about 25% of a morphology preservative. In another embodiment, the fixation solution is comprised of about 5% to about 15% of a morphology preservative. In a preferred embodiment, the fixation solution is comprised of about 10% of a morphology preservative.

In some embodiments, a permeation enhancer is added to the sample during the fixation step and/or the dehydration step. The permeation enhancer accelerates the access of dye to the deeper portion of the sample, while overall improving the dyeing process. The permeation enhancer also accelerates the penetration of fixative, dehydrant, and/or clearing agent. Non-limiting examples of permeation enhancers include acids such as acetic acid, methacarn comprising acetic acid, sulphoxides such as dimethylsulfoxide (DMSO), azone, pyrrolidones, propylene glycol, fatty acids, essential oils, phospholipids, s-collidine, and surfactants such as Tween. In one embodiment, the fixation solution is comprised of about 0% to about 75% of a permeation enhancer. In another embodiment, the fixation solution is comprised of about 10% to about 50% of a permeation enhancer. In a preferred embodiment, the fixation solution is comprised of about 30% of a permeation enhancer.

In some embodiments, the permeation enhancer is at least one acid. In some embodiments, the acid is an organic acid. Non-limiting examples of organic acids include acetic acid, glacial acetic acid, lactic acid, propionic acid, butyric acid, succinic acid, citric acid, 3-hydroxypropionic acid, glycolic acid, or formic acid. In one embodiment, the acid is acetic acid. Acetic acid is useful for enhancing the speed of fixation, which is important for rapid sample processing, while also significantly improving the quality and depth of images from cleared samples using any type of sectioning image modalities. Acetic acid is also useful for lysing red blood cells, which allows for removal of heme pigment, which is a significant deterrent to clarity of the sample by virtue of its broad light absorption characteristics in the typical workable wavelength range of routine fluorescent imaging. In one embodiment, the step of fixing the sample further comprises the addition of a lysing agent to the sample. In a particular embodiment, the step of fixing the sample further comprises the addition of a red blood cell lysing agent to the sample. In another embodiment, the step of dehydrating the sample further comprises the addition of a lysing agent to the sample. In another embodiment, the fixative solution further comprises a red blood cell lysing agent. In a preferred embodiment, the red blood cell lysing agent is acetic acid. In other embodiments, the acid is an inorganic acid. The solution may further be comprised of at least one organic solvent. Non-limiting examples of organic solvents include methanol, absolute methanol, chloroform, dichloromethane, ethanol, isopropanol, acetone, ethyl acetate, acetonitrile, hexane, hexene, octane, pentane, cyclohexane, iso-octane, xylene (ortho, meta, or para), and 1-hexene. In one embodiment, the organic solvent is absolute methanol. Methanol is useful for tissue processing by arresting enzymatic function and degradation while maximally preserving genetic and proteomic information. In another embodiment, the organic solvent is chloroform. In one embodiment, the solution is comprised of two organic solvents and an acid. As a non-limiting embodiment, the fixative solution is comprised of about 60% absolute methanol, about 30% chloroform, and about 10% glacial acetic acid, which is also known as methacarn. When in combination with fluorescent dyes and clearing, methacarn may be useful for deep fluorescent tissue section imaging of human samples for histologic evaluation, and for creating the contrast needed for accurate histologic evaluation.

The fixation step may be performed under any condition that promotes rapid tissue processing, such as conditions that increase the rates of chemical reaction and diffusion, as would be understood by one of ordinary skill in the art. In some embodiments, the fixation step is performed at an elevated temperature. As used herein, the term "elevated temperature" refers to temperatures above those experienced in the earth's atmosphere, preferably above 30° C. In one embodiment, the elevated temperature ranges from about 20° C. to about 75° C. In another embodiment, the elevated temperature ranges from about 35° C. to about 50° C. In another embodiment, the elevated temperature is about 45° C. In a non-limiting example, the fixation, dehydration, and/or staining is performed under microwave irradiation for the purpose of accelerating diffusion, chemical reaction, or temperature.

The fixation step can be performed for any suitable length of time. The length of time can generally be any length of time suitable for preserving the sample. In certain embodiments, the period of time may be from about 1 minute, about 5 minutes, about 15 minutes, about 30 minutes, about 1 hour, about 2 hours, about 3 hours, about 4 hours, about 5 hours, about 6 hours, about 12 hours, or about 24 hours. In one embodiment, the fixation step is performed over a period of time about 1 hour. In another embodiment the fixation step is performed over about 12 to 16 hours. In another embodiment the fixation step is performed over the course of weeks to years.

In one embodiment, the method of the present invention comprises the step of simultaneously fixing, dehydrating, and staining the sample by contacting the sample with a dehydration solution comprised of at least one dehydrant and at least one fluorescent dye. In another embodiment, the method of the present invention comprises the step of simultaneously dehydrating and staining the sample by contacting the sample with a dehydration solution comprised of at least one dehydrant and at least one fluorescent dye.

In another aspect, the method of the present invention further comprises the step of clearing the sample. Clearing the sample provides increased depth and clarity of imaging of the sample. In one embodiment, the clearing step is performed in absence of a fixation step. In some embodiments, the step comprises clearing the sample by contacting the sample with a clearing solution. As a non-limiting embodiment, the sample is cleared by replacing water with a clearing solution that has a higher refractive index than water that more closely resembles that of proteins and organelles, thereby drastically reducing light scattering and enabling imaging depths of millimeters instead of micrometers. In one embodiment, the clearing solution is comprised of at least one solvent. Any solvent may be used in the clearing solution, as long as the overall refractive index of the clearing solution is higher than the refractive index of water and the solvent does not damage the morphology of cellular components of the sample. In one embodiment, the refractive index of the clearing solution ranges from about 1.4 to about 1.6. In another embodiment, the refractive index of the clearing solution ranges from about 1.33 to about 1.49. In another embodiment, the refractive index of the clearing solution is greater than about 1.4. In another embodiment, the refractive index of the clearing solution is greater than about 1.5. In one embodiment, the clearing solution is further comprised of an agent that is water soluble and has a high refractive index.

In some embodiments, the solvent is an organic solvent. Non-limiting examples of organic solvents useful as clearing agents include, benzyl alcohol, benzyl benzoate, xylene, limonene, benzene, toluene, chloroform, petroleum ether, carbon bisulfide, carbon tetrachloride, dioxane, glycerol, sugar solutions, dibenzyl ether, clove oil, and cedar oil. In one embodiment, the solvent is benzyl alcohol. In another embodiment, the solvent is benzyl benzoate. In another embodiment, the solvent is xylene. In another embodiment, the solvent is glycerol. In another embodiment, the solvent is a sugar solution. In another embodiment, the solvent is dibenzyl ether. In another embodiment, the solvent is hexane.

In some embodiments, the clearing solution is comprised of a first solvent and a second solvent. In one embodiment, the ratio of the first solvent to the second solvent ranges from about 100:1 to about 1:100. In another embodiment, the ratio of the first solvent to the second solvent ranges from about 10:1 to about 1:10. In another embodiment, the ratio of the first solvent to the second solvent ranges from about 5:1 to about 1:5. In a preferred embodiment, the ratio of the first solvent to the second solvent is about 1:2. In some embodiments, the solvent is an organic solvent. In a particular embodiment, the clearing solution is comprised of benzyl alcohol and benzyl benzoate. In one embodiment, the ratio of benzyl alcohol to benzyl benzoate is about 1:2.

The clearing step may be performed under any condition that promotes rapid clearing of the sample, as would be understood by one of ordinary skill in the art. In some embodiments, the clearing step is performed at an elevated temperature. In one embodiment, the elevated temperature ranges from about 20° C. to about 75° C. In another embodiment, the elevated temperature ranges from about 35° C. to about 50° C. In another embodiment, the temperature is about 22° C.

The clearing step can be performed for any suitable length of time. The length of time can generally be any length of time suitable for achieving sufficient reduction in light scattering to enable imaging to the desired depth in the sample. In certain embodiments, the period of time may be from about 1 minute, about 5 minutes, about 10 minutes, about 15 minutes, about 30 minutes, about 1 hour, about 2 hours, about 3 hours, about 4 hours, about 5 hours, about 6 hours, about 12 hours, or about 24 hours. In one embodiment, the clearing step is performed in about 10 minutes to about 1 hour. In one embodiment, the clearing step is performed in about 30 minutes. In one embodiment, the clearing step is performed in about 12 hours.

In one embodiment, the clearing step is further comprised of the step of adding a solvent to the sample prior to adding the clearing solution. In some embodiments, the solvent is an organic solvent. In one embodiment, the solvent is an alcohol. The alcohol is useful for dehydrating the sample. Non-limiting examples of alcohols include methanol, ethanol, propanol, isopropanol, butanol, isobutanol, ethyl butanol, t-butanol, dioxane, ethylene glycol, acetone, and amyl alcohol. In a preferred embodiment, the solvent is methanol. In one embodiment, the solvent is added in combination with a permeation enhancer. Non-limiting examples of permeation enhancers include acetic acid, polyethylene glycol (PEG), mono- and dimethyleneglycol, propylene glycol, polyvinyl pyrrolidone, or the like, surfactants such as dimethyl sulfoxide (DMSO), polyoxyethylene sorbitan esters (e.g., TWEEN such as TWEEN 80), sodium dimethyl sulfosuccinate, mild household detergents, or the like. In one embodiment, the permeation enhancer is selected from the group consisting of acetic acid, DMSO, and TWEEN. The addition of a solvent in combination with a permeation enhancer increases the rate of clearing with BABB by improving miscibility and permeability, and also eliminates the need for gradual gradient steps of decreasing alcohol concentration.

In part, the present invention provides a method of rapidly processing a tissue sample. The length of time can generally be any length of time suitable for fixing the sample and clearing the sample. In certain embodiments, the period of time may be from about 1 minute, about 5 minutes, about 10 minutes, about 15 minutes, about 30 minutes, about 1 hour, about 2 hours, about 3 hours, about 4 hours, about 5 hours, or about 6 hours. In one embodiment, the steps of fixing the sample and clearing the sample are performed in about 1 hour to about 2 hours. In one embodiment, the steps of fixing the sample and clearing the sample are performed over a period of time about 1.5 hours.

In another aspect, the method of the present invention further comprises the step of imaging the sample. In one embodiment, the step of imaging the sample further comprises producing a visual image of the tissue sample. The sample may be imaged using any imaging method compatible with the sample processing methods described herein. Preferred imaging methods include fluorescence based sectioning imaging methods. Contrary to destructive 3-D histology approaches such as pigmented plastic embedding systems and whole slide imaging (WSI), these fluorescence based methods are non-destructive, allowing for the preservation of samples for ancillary studies such as immunostains and molecular studies. Examples of fluorescence based sectioning imaging methods include, but are not limited to, multiphoton microscopy (MPM), side-plane illumination microscopy, traditional confocal microscopy, spinning disk confocal microscopy, structured illumination microscopy, and the like. In animal tissue (Parra et al., 2010, J. Biomed. Opt. 15:036017-036017-5; Vesuna et al., 2011, J. Biomed. Opt. 16:106009-106009-6; Fu et al., 2009, Gastroenterology 137:453-465), the depth of imaging can be increased over samples prepared using more traditional methods, such as formalin fixing, by combining MPM with optical clearing. In one embodiment, the sample is imaged using multiphoton microscopy (MPM). In another embodiment the sample is imaged using confocal microscopy. In another embodiment the sample is imaged using selective plane illumination microscopy. In another embodiment the sample is imaged using deconvolution microscopy. In another embodiment the sample is imaged using super-resolution microscopy. In one embodiment, the method of imaging a tissue sample comprises the steps of obtaining a tissue sample, contacting the tissue sample with a fixative solution comprising at least one fluorescent dye, contacting the tissue sample with a clearing solution, and producing a tissue sample image by measuring intensity values of the fluorescence of the tissue sample, and converting the intensity values to effective optical densities, such that the optical densities recreate the coloration of a stain in a produced image of the tissue sample.

The imaging methods of the present invention provide a method for image analysis that allows reproduction of images essentially indistinguishable from traditional histology stains. In one embodiment, the method involves a multichannel approach, wherein intensity values of fluorescence from the sample are converted to optical densities using an exponential pseudo-coloring process, which is an inversion of a logarithmic pseudo-coloring process, wherein intensity values of fluorescence are converted to optical densities in red, green, and blue channels. In one embodiment, the step of imaging the sample further comprises the steps of measuring intensity values of the fluorescence of the sample, and converting the intensity values to effective optical densities recreate the coloration of a stain in the sample image. In one embodiment, the intensity values of one or more fluorescence channels are converted to effective optical densities in one or more pseudo-color display channels using an exponential pseudo-coloring process, wherein the equation that results in optical densities includes a constant to the power of the intensity values from fluorescence, as would be understood by one of ordinary skill in the art. Numerically:

$$Ch1 = C_1\hat{}(a_1 N + b_1 P)$$

$$Ch2 = C_2\hat{}(a_2 N + b_2 P)$$

$$Ch2 = C_2\hat{}(a_3 N + b_3 P)$$

where Ch1, Ch2, Ch3 are color display channels, such as Red, Green and Blue; $C_1$, $C_2$, $C_3$ are positive constants; $a_1$, $a_2$, $a_3$, $b_1$, $b_2$, $b_3$ are constants that may be positive or negative; and N and P are fluorescence intensities recorded from different fluorescence channels. In one embodiment, the intensity values are converted to effective optical densities using an exponential pseudo-coloration process.

For an example of a logarithmic color deconvolution process, see Ruifrok and Johnston, 2001, Anal. Quant. Cytol. Histol. 23:291-299, which is incorporated by reference herein in its entirety.

In one embodiment, the fluorescence is intrinsic fluorescence from the sample. In another embodiment, the fluorescence is fluorescence from the fluorescent dye. In one embodiment, the fluorescent dye is a nuclear dye. In another embodiment, the fluorescent dye is a protein dye. The number of channels used may be varied as needed to achieve the desired image, as would be understood by one skilled in the art. In one embodiment, the number of channels is two channels. In a specific embodiment, the two channels are an intrinsic fluorescence channel and a fluorescent nucleic acid dye channel. In another embodiment, the two channels are a fluorescent nucleic acid dye channel and a fluorescent protein staining channel. In a non-limiting example, the intrinsic fluorescence, emanating primarily from cross-linked proteins and corresponding to the staining typically achieved by protein stains such as eosin, can be augmented by use of formalin as the fixative, a feature that facilitates the reproduction of normal coloration by improving signal to noise of this channel and facilitating separation from nucleic acid fluorescence.

The imaging method of the present invention also provides images of samples that mimic common pathology stains, resulting in the accurate and efficient interpretation of the images. Examples of pathology stains which can be reproduced using the methods of the present invention include, but are not limited to, hematoxylin, eosin, wright, giemsa, Masson's trichrome, Jones, trichrome, periodic acid Schiff(PAS) and reticulin stains. Combinations of pathology stains can also be reproduced using methods of the present invention. In one embodiment, the combination of pathology stains is hematoxylin and eosin (H&E). In another embodiment, the combination of pathology stains is wright and giemsa.

In some embodiments, the step of imaging the sample is performed in combination with an additional imaging method, resulting in multi-modal imaging. In one embodiment, the additional imaging method is a higher-order harmonic generation. Higher-order harmonic generation permits the recreation of additional specialized histological stains, such as collagen stains like trichrome and silver stains like Jones stain. In one embodiment, the higher order harmonic generation is second harmonic generation (SHG). SHG evolves from multiphoton excitation of asymmetric repeating proteins such as collagen, and may be used for simple identification and quantification of collagen fibrosis and amyloid in combination with the imaging method, such as MPM. In one embodiment, the additional imaging method is Fluorescence Lifetime Imaging. Fluorescence Lifetime Imaging may be used to provide additional contrast in MPM by distinguishing between intrinsic fluorophores with differing lifetime characteristics. In another embodiment, the additional imaging method uses multiple fluorescent antibodies. Multiple fluorescent antibodies may be used to provide potential for performing immunohistochemistry in uncut samples with multiple antigens detectable on the same cells. In another embodiment, the imaging method is used in combination with diode lasers. See Dechet et al., 2003, J. Urol. 169:71-74 and Durfee et al., 2012, Opt. Express 20:13677-13683, each which is incorporated by reference herein in its entirety. Other techniques known in the art to increase the rate of scanning of the sample image may be used in the imaging step, as would be understood by one of ordinary skill in the art. Non-limiting examples include multibeam scanning systems, spatiotemporal multiplexing, and temporal focusing. See Bewersdorf et al., 1998, Opt. Lett. 23:655-657, Amir et al., 2007, Opt. Lett. 32-1731-1733, Oron et al., 2005, Opt. Express 13:1468-1476, and Zhu et al., 2005, Opt. Express 13:2153-2159, each which is incorporated by reference herein in its entirety. In another embodiment, the imaging step is performed in real time using video imaging.

The methods of the present invention provide a high depth sample image, wherein a clear, high-quality image of the sample is obtained at a greater sample depth as compared with more traditional histological methods, such as formalin fixation. In one embodiment, the sample image is obtained at a sample depth of about 100 nm to about 2 cm. In another embodiment, the sample image is obtained at a sample depth of about 100 nm to about 500 µm. In another embodiment, the sample image is obtained at a sample depth of about 100 nm to about 1 cm. In another embodiment, the sample image is obtained at a sample depth of about 200 µm to about 500 µm. In another embodiment, the sample image is obtained at a sample depth of about 100 nm to about 100 µm. In another example, the sample image is obtained at a sample depth of about 200 µm.

In one embodiment, imaging of the sample provides digital sample data. This digital data may then be stored for later distribution, such as for consultation and health records, thereby improving the accessibility of the images for further evaluation or reevaluation. In addition, digital sample data is capable of maintaining the integrity of the data, as opposed to physical samples which may be lost or damaged and cannot be stored digitally.

In one embodiment, the sample image is a three dimensional (3-D) sample image. A 3-D sample image can be produced using any method known in the art, as would be understood by one skilled in the art. In one embodiment, the 3-D sample image is produced from an entire biopsy. In another embodiment, a 3-D sample image produced from a whole biopsy provides a quantitative approach to diagnosing a disease. In another embodiment, a 3-D sample image of the present invention provides facile identification of subtle morphologic findings in the imaging sample. For example, 3-D sample images improve the quantitative and qualitative analysis of fibrosis observed in various conditions such as cirrhosis, hypertensive renal disease, interstitial lung disease, and ovarian cancer over other two-dimensional (2-D) histological methods currently known in the art. In another embodiment, a 3-D sample image of the present invention is used to diagnose a malignant growth. In one embodiment, the methods of the present invention provide full rotational control of 3-D sample images. Diagnosis of malignant growth is often dependent on visualizing growth patterns, particularly in glandular-based disorders such as prostate and breast cancer. Such analysis has been primarily based on the two-dimensional orientation, which may require pathologists to look back-and-forth at (hopefully) contiguous segments in order to render a diagnosis. In these 2D methods, visual inspection can be further complicated by poor embedding and orientation differences of the sample. In non-limiting examples, the 3-D sample images of the present invention are used to diagnose colon cancer in liver and for the diagnosis of endometrial abnormalities. In another non-limiting example, 3-D reconstructions of MPM imaging from clarified tissue may be used on complete biopsy-sized tissue specimens and may also be used to produce quantifiable characterization of collagen fibrosis. Other non-limiting examples of the use of 3-D sample image include identification of low-grade abnormalities in glandular cell growth, such as with prostate and breast neoplasia, the evaluation of depth of invasion of tumors, such as for determining depth of muscle invasion in bladder biopsies, and the more complete quantitative evaluation of fibrosis, of particular significance in kidney and liver biopsies.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

High-Resolution, 2- and 3-Dimensional Imaging of Uncut, Unembedded Tissue Biopsy Samples The results described herein demonstrate that the combination of clearing agents and fluorescent dyes is useful for clinical application of multiphoton imaging of complete biopsy specimens, along with added informational content from SHG. Excellent cellular contrast can be achieved from both intrinsic fluorescence and with extrinsic nucleic acid dyes. Multichannel imaging facilitated a pseudocolorization process that mimicked the appearance of traditional stains. Three-dimensional reconstructions of MPM imaging from clarified tissue may be used on complete biopsy-sized tissue specimens and may also be used to produce quantifiable characterization of collagen fibrosis.

The materials and methods employed in these experiments are now described.

Tissue Clearing and Staining

Human tissue specimens were obtained from discarded pathologic tissue of liver, kidney, breast, and prostate resections. Samples had been fixed in 4% formaldehyde solution before clearing for a variable period of time ranging from hours to days. Random tissue sections of approximately 1 cm×5 mm×2 mm were immersed directly in methacarn containing 10 uM DAPI and 0.5% by volume eosin for 1 hour. Subsequently samples were immersed in benzyl alcohol/benzyl benzoate in a 1:2 ratio for 1 hour.

Imaging

Multiphoton images, including intrinsic fluorescence, nuclear fluorescent staining, and SHG, were obtained by using a custom home-built microscope based on a tunable 80-MHz-pulsed Ti:Sapphire laser (Mai Tai, Spectra-Physics, Mountain View, Calif.), a 3-axis motorized microscope stage (ASI Imaging, Eugene, Oreg.), and an Olympus BX51 upright microscope head fitted with an ×5 Nikon objective with a numerical aperture of 0.5 (AZ-Plan Fluor 5×, Nikon Corp, Tokyo, Japan).

Both intrinsic and nucleic acid dye fluorescence were generated by using 740-nm incident light with a pulse width of 100 fsec. A 500-nm wavelength dichroic mirror separated intrinsic from exogenous fluorescence, both detected by using photomultiplier tubes (H7422, Hamamatsu, Bridgewater, N.J.). The microscope head incorporates a modified optical collection filter box to accommodate the photomultiplier tubes. Second-harmonic generation was collected in transmission by using a 370/20 bandpass filter (Chroma Technologies, Rockingham, Vt.). An adjustable 3-axis mount (New Focus, Santa Clara, Calif.) was used to manually position the SHG photomultiplier tube (Hamamatsu HC-125-02).

Control and image collection were performed with the use of ScanImage software (Howard Hughes Medical Institute, Janelia Farm Research Campus, Ashburn, Va.)(Pologruto et al., 2003, Biomed. Eng. Online 2:13). Focusing was done at 512×512 resolution with 1 millisecond per line scan times, giving a frame rate of approximately 2 frames per second. Image resolution at collection was 2056×2056 or 1024×1024 at a zoom factor of 1 to 6, depending on desired magnification. Between 4 and 8 frames were averaged per slice for a total acquisition time of 20 seconds per slice. Incident laser intensity was manually adjusted via a Pockels cell in the excitation pathway. Stacks were collected in 1- to 5-µm steps at 16-bit depth and processed by using ImageJ software (developed at the National Institutes of Health, Bethesda, Md.). Total imaging time for 1 mm cube reconstructions was approximately 6 hours. Post-image processing involved conversion to 8-bit, image inversion, manual global contrast adjustment using the built-in "brightness/contrast" plug-in on a random sample section, and application of the built-in "smooth" function.

Pseudo-coloring was performed by inverting the matrix conversion process presented by Ruifrok and Johnston (Ruifrok and Johnston, 2001, Anal. Quant. Cytol. Histol. 23:291-299). Briefly, intensity values from intrinsic fluorescence and nuclear stains were converted to optical densities in red, green, and blue channels according to the published matrix values for H&E by using MATLAB (MathWorks, Natick, Mass.). Intrinsic fluorescence intensity was assigned to the eosin channel (E) while nucleic acid stains were assigned to the hematoxylin channel (H). Following image normalization and scaling to achieve adequate contrast, the red (R), green (G), and blue (B) channel values for the combined pseudocolored images were calculated as follows:

$$R = 10^{-(0.644E+0.093H)}$$

$$G = 10^{-(0.717E+0.954H)}$$

$$B = 10^{-(0.267E+0.283H)}$$

Traditional Histology

Paraffin embedding, sectioning, and H&E staining were performed by using established techniques with a Tissue-Tek VIP tissue processor (Sakura, Torrance, Calif.). Immunohistochemical stains for cytokeratin (CK) 7 and CK20 used commercial antibodies and were performed with standard commercial immunohistochemistry equipment (Dako, Glostrup, Denmark).

The results of the experiments are now described.

Clearing allowed imaging with excellent cellular and nuclear resolution of SYTOX Green or acridine orange-stained specimens more than 500 µm deep into formalin-fixed human prostate, liver, breast, and kidney samples (FIGS. 2-3). Multiphoton images showed readily identifiable features, comparable to cut slices of H&E-stained tissue, that were amenable to visual pathologic diagnosis without additional morphology training. Normal prostatic glandular structure was readily visualized with adequate nuclear detail (FIG. 3A). Similarly, high-power views of liver tissue produced recognizable chromatin patterns and cytoplasmic detail (FIG. 3B). Breast virtual sectioning showed distinguishable tubular and glandular organization (FIG. 3C). Kidney samples showed clear glomerular structure and visible nuclear and cellular detail in adjacent tubules (FIG. 3D). Clearing was most complete in less cellularly dense tissues such as breast and prostate, but with the BABB clearing protocol even kidney and liver cleared sufficiently to show good morphologic detail 1 mm deep into formalin-fixed tissue.

Figure 5:
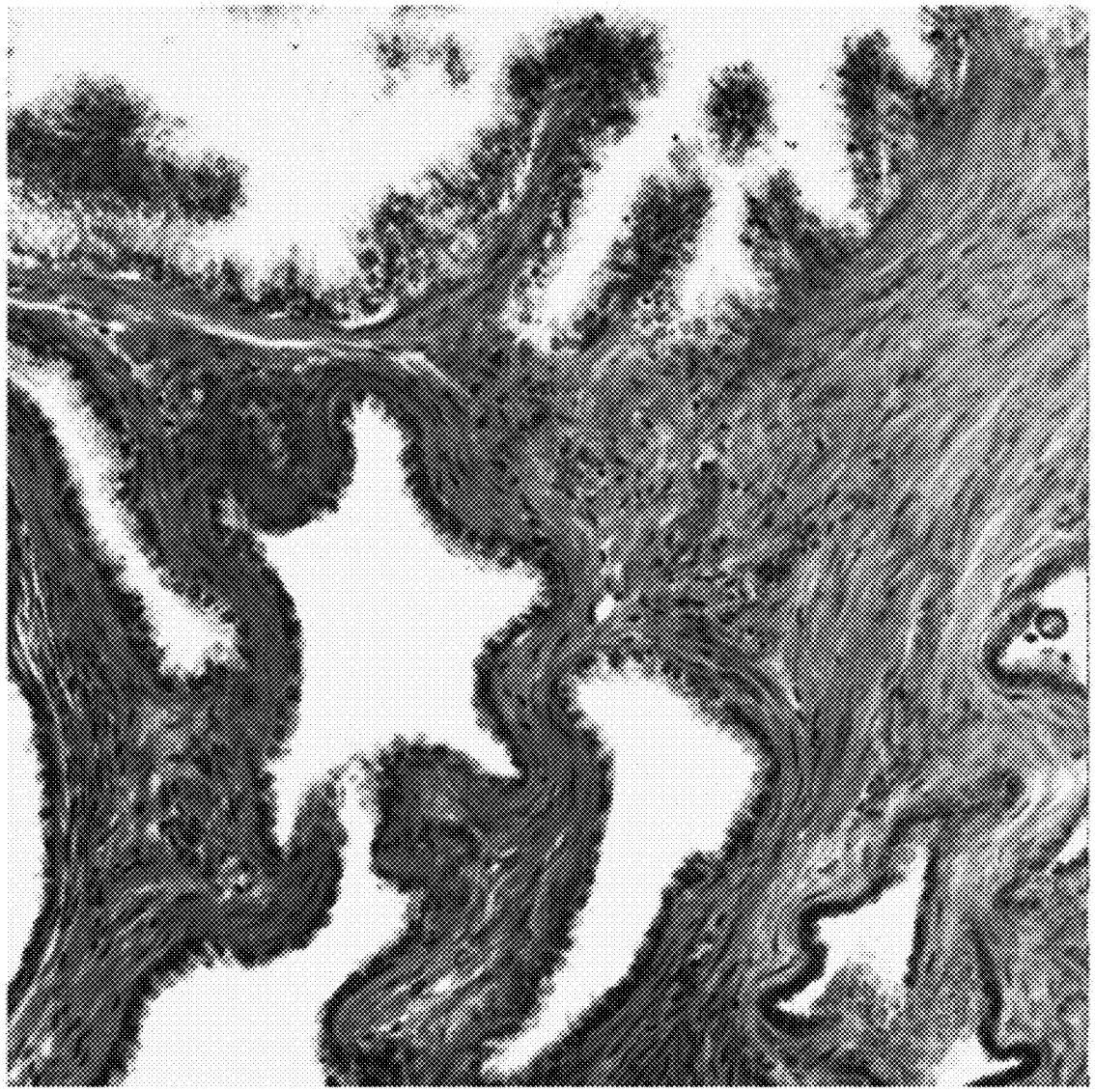
FIG. 5 is an image demonstrating pseudo-colorization. Prostate section obtained with multiphoton microscopy on cleared tissue with SYTOX Green at depth of approximately 500 µm (as in FIG. 4), processed to mimic hematoxylin-eosin section.
Figure 6A:
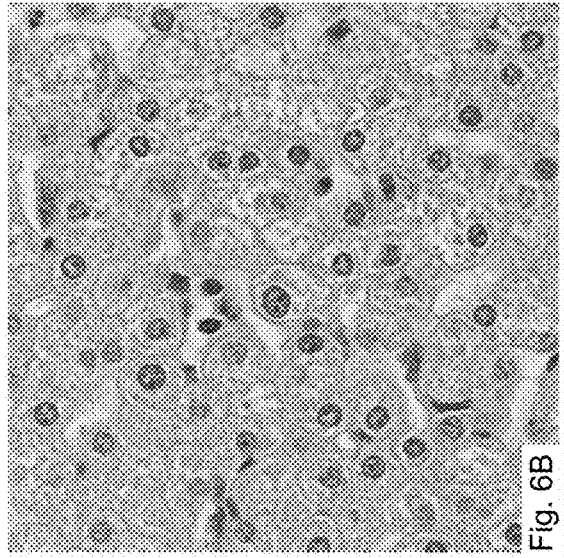
FIGS. 6A-6D, depicts hematoxylin-eosin (H&E)-stained images post multiphoton microscopy (MPM) of clarified tissue. Sample sections from the same specimens depicted in FIG. 3, including prostate (FIG. 6A), liver (FIG. 6B), breast (FIG. 6C), and kidney (FIG. 6D), show no perceptible degradation or other visual change with traditional wax embedding, cutting, and H&E staining after clarification of tissue and MPM imaging (original magnifications ×20 [FIGS. 6A, 6C, and 6D] and ×50 [FIG. 6B]).
Figure 6B:
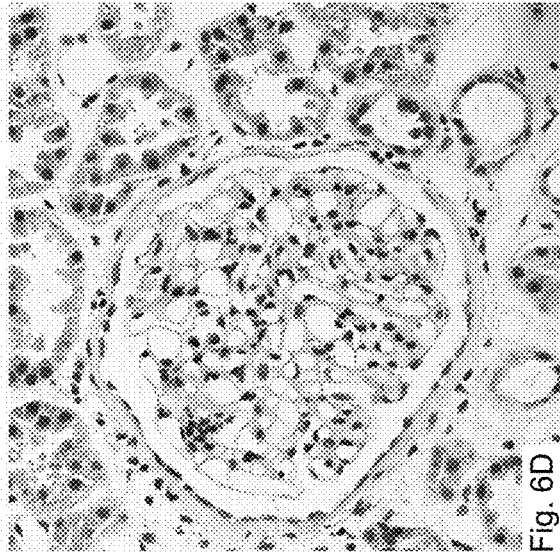
Figure 6C:
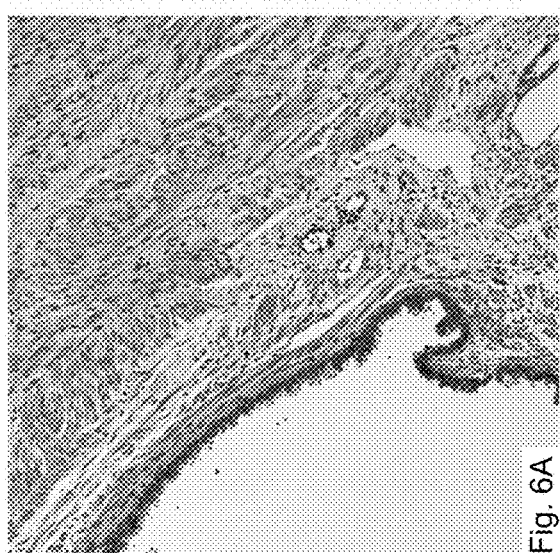
Figure 6D:
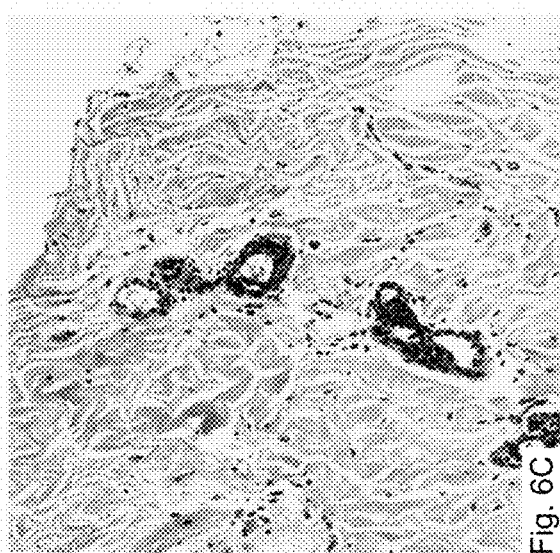

Multiphoton laser excitation and use of a fluorescent nuclear dye also allowed isolation of cytoplasmic, nuclear, and collagen components of the specimens. For example, as illustrated with kidney images presented in FIG. 4, intrinsic fluorescence corresponded to the cellular structure and allowed clear evaluation of the glomerular vasculature and tubular cellular organization (FIG. 4A). The nucleic acid stain channel allowed independent evaluation of nuclei (FIG. 4B). Combining these 2 channels with the SHG by intervening collagen strands (pseudocolored in red) allowed clear visualization of the low-level collagen banding that is present in normal human kidney (FIG. 4C). It was also possible to replicate H&E-type coloration on fluorescently stained sample images obtained with MPM (FIG. 5). The multiple channels could be individually matched to corresponding hues that mimic the effect of H&E.

Figures 7A, 7B:
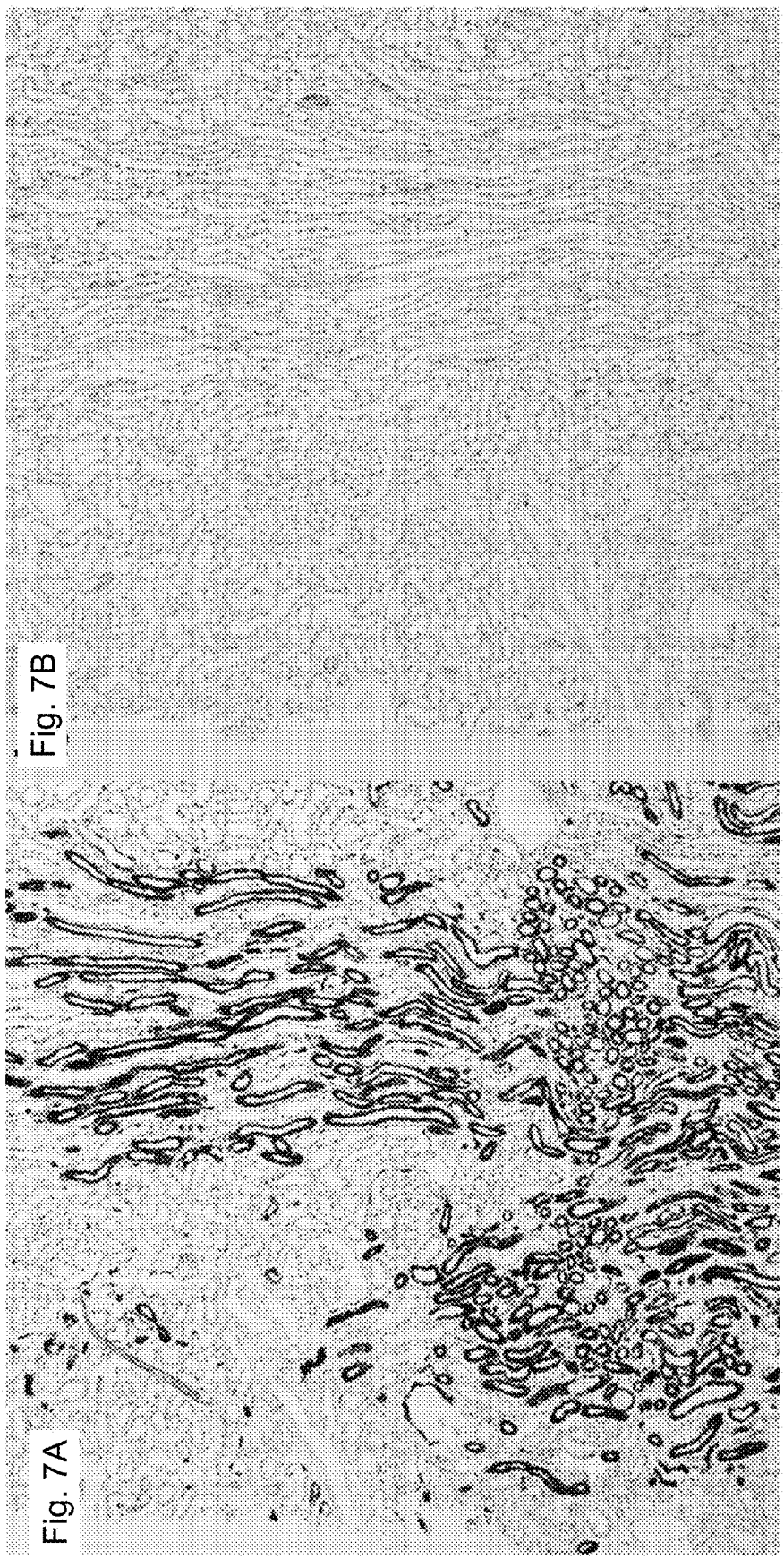
FIGS. 7A-7B, depicts images demonstrating examples of compatibility of benzyl alcohol/benzyl benzoate clearing and SYTOX Green staining with traditional immunohistochemistry on human renal tissue.

Clearing and fluorescent staining did not have any detectable effect on the subsequent paraffin embedding, sectioning, and H&E staining of the tissues. The same specimens shown in FIG. 3 were further processed by traditional histologic techniques and showed no identifiable morphologic adverse effects (FIG. 6). In addition, immunohistochemical staining of kidney tissue for CK7 and CK20 showed the expected specificity of CK7 for descending medullary renal tubules without binding of CK20 (FIG. 7). Thus, the sensitivity and specificity of these antibodies were clearly maintained after the use of BABB as a clearing agent and SYTOX Green or acridine orange as a fluorescent nuclear stain.

Figure 8A:
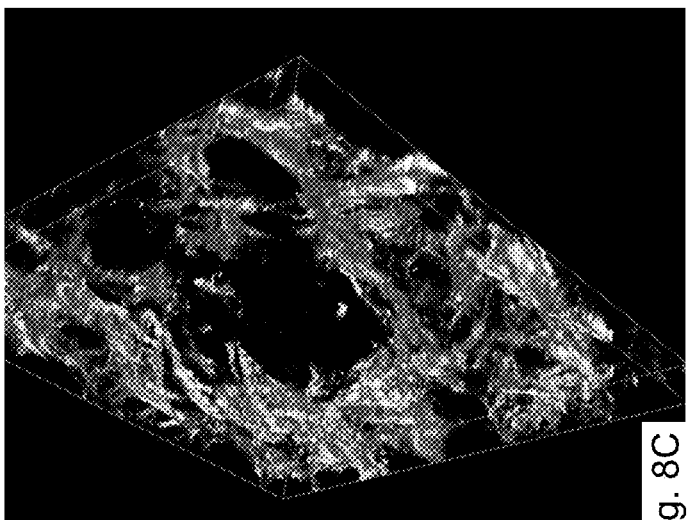
FIGS. 8A-8C, depicts representative large block 3-D reconstructions of normal human tissue.
Figure 8B:
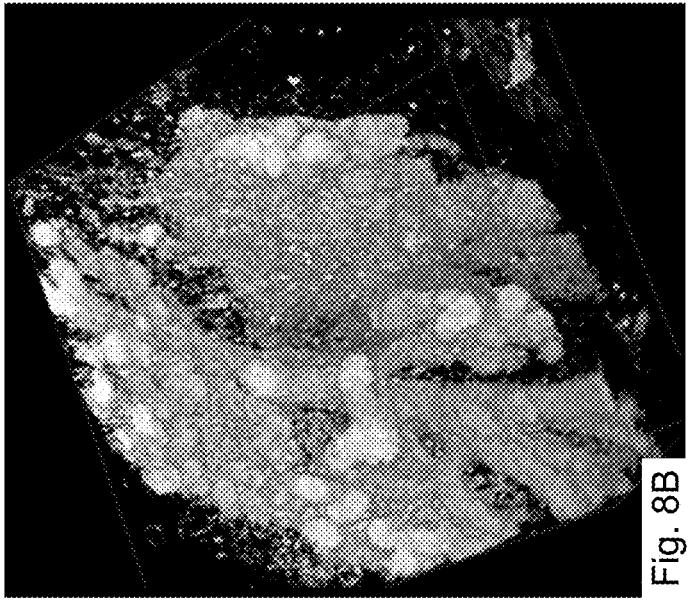
Figure 8C:
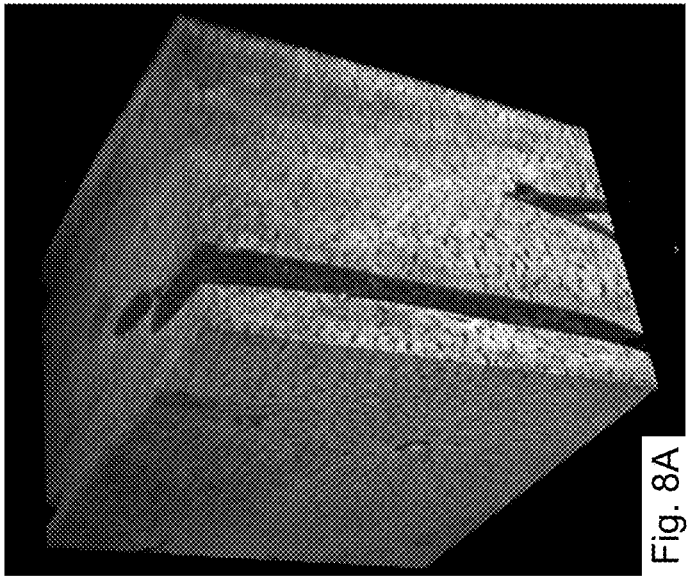

The acquisition of digital images also allowed 3-dimensional reconstruction of 1-mm-thick blocks of tissue. Full-scale 3-D reconstructions of intrinsic fluorescence of liver provide a more complete perspective on normal tissue growth, as illustrated in the liver reconstruction presented in FIG. 8A. The potential for accurate evaluation of neoplastic growth margins is apparent. Nuclear fluorescence scans taken every 4 µm also allowed visualization of the arborizing structure of breast glands as noted in FIG. 8B. The transparency of collagen fibers and fat to the nuclear dye wavelengths facilitated these large set reconstructions, which could be easily rotated and manipulated with the ImageJ 3-D volume-rendering plug-in on a standard 64-bit laptop computer. In addition, 3-dimensional reconstructions of SHG signal in liver and kidney (FIG. 8C) demonstrate the ability to perform complete specimen quantitative analysis of fibrosis without the need for additional tissue processing. As expected, SHG was brighter toward the portion of the tissue distal to laser excitation (closest to detector), but produced resolved collagen detail throughout 1-mm-thick tissue.

Traditional techniques of fixation with formalin with physical wax embedding and microtome sectioning for histology have been successfully used in routine pathology evaluation for more than a century. Part of their success can be attributed to the ease of use and forgiving nature of formalin fixation, coupled with the compatibility of wax embedding with a range of simple and inexpensive staining techniques. Other important factors for the continued success of formalin-fixed, wax-embedded slides have been the long-term preservation that formalin fixation affords and the cumulative experience of pathologists, which increases the accuracy and consistency of interpretation.

Nonetheless, there remain considerable limitations associated with current specimen processing methods and the evaluation of these by pathologists. For biopsies, these include the limited amount of tissue that is typically directly visualized, a function of both the desire to preserve tissue for ancillary testing and the time required to inspect multiple slides. Not infrequently, additional tissue evaluation is needed, but requests for recuts and levels delay diagnoses. Also, they usually still result in sampling only a portion of the tissue while reducing tissue availability for increasingly important immunostaining and molecular analysis. In addition, imperfect embedding results in tissue waste and can hamper interpretation, and the cutting process itself produces artifacts that may hinder evaluation. Imaging of unembedded and uncut tissue addresses these traditional processing limitations. It provides the opportunity to visualize entire biopsy specimens, reducing the likelihood of missing important features owing to incomplete sampling, and to preserve tissue for ancillary tests.

Other advantages of analyzing uncut, unembedded specimens relate to savings in time and effort. Embedding, cutting, and staining are some of the most time-consuming and manual steps in tissue processing (Busea, 2007, Ann. Diagn. Pathol. 11:206-211; Hassell et al., 2010, BMC Clin. Pathol. 10:2; Busea, 2009, Ann. Diagn. Pathol. 14:107-124), requiring personnel with significant expertise. While automation and microwave-based tissue processing have allowed some sites to begin to offer same-day diagnosis for some biopsy samples, the post-dehydration and clearing steps are an impediment in satisfying an increasing need on the part of providers and patients for rapid turnaround of morphologic evaluation.

Another aspect of interest in tissue biopsy evaluation that was explored is the visualization of 3-dimensional structure. Previous attempts at creating large 3-D data sets from tissue have used methods producing poor contrast, poor depth penetration, or that successively remove tissue as the 3-D volume is imaged (Zysk et al., 2007, J. Biomed. Opt. 12:051403-051403-21; Bizheva et al., 2005, J. Biomed. Opt. 10:11006-11006-07; Ragan et al., 2007, J. Biomed. Opt. 12:014015-014015-9; Dechet et al., 1999, J. Urol. 162:1282-1284). Thus, past 3-D reconstruction techniques failed to improve upon the most important limitations of traditional histology. However, 3-D reconstructions of clarified tissue using MPM showed excellent cellular contrast, sufficient depth, such that entire biopsy specimens could be imaged, and compatibility with subsequent traditional processing, including preservation of immunostain capability with the few antibodies tested.

A critical barrier to clinical adoption of new imaging technologies is resistance from pathologists who have spent years honing their skills on a specific set of specialty stains and the desire to maintain full compatibility with established clinical practice. The MPM/clearing approach has produced images that have resolution and fields of view similar to those of current routine practice and provide contrast similar to that obtained with commonly used histologic stains, but that allow subsequent traditional processing without apparent adverse effects. The multichannel method described herein also allowed straightforward pseudo-colorization that represents morphology in a method analogous to traditional stains, allowing pathologists to easily recognize salient histologic features.

Example 2

Exemplary Tissue Staining Protocol

Figure 15:
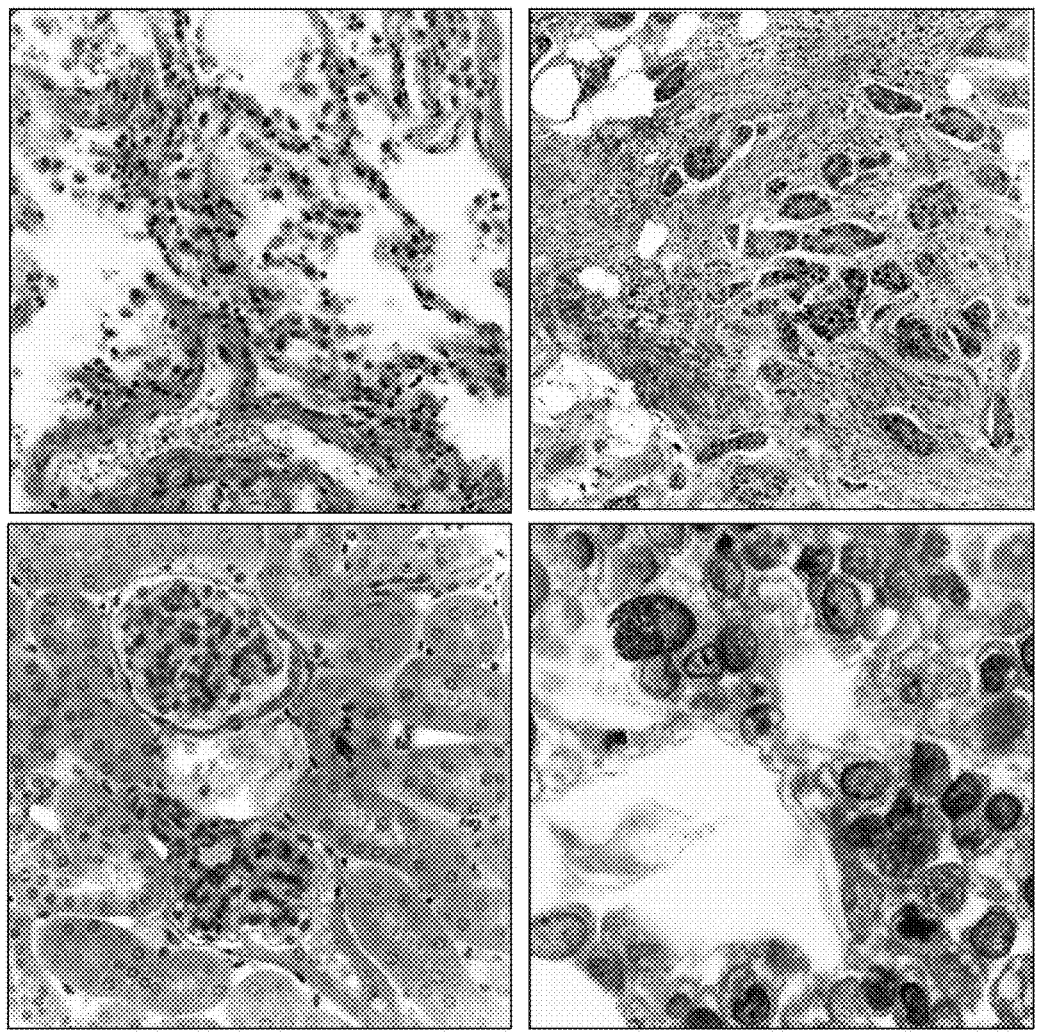
FIG. 15 depicts a series of images of tissue samples prepared using methods of the present invention.

A core biopsy-sized tissue specimen is fixed in formalin for a period of time from 20 minutes to 4 weeks. The specimen is then placed directly in a solution of methacarn which has 10 µM DAPI and 0.5% by volume eosin added to the solution. The specimen is incubated at 45° C. for 60 minutes. The specimen is transferred directly to a solution of 100% BABB, and incubated for 30 minutes. The specimen is imaged in a BABB bath. FIG. 15 depicts images of tissue samples prepared according to this exemplary method.

Example 3

Exemplary Tissue Staining Protocol

A core biopsy-sized tissue specimen is placed directly in a solution of methacarn which has 10 µM DAPI and 0.5% by volume eosin added to the solution. The specimen is incubated at 45° C. for 60 minutes. The specimen is transferred directly to a solution of 100% BABB, and incubated for 30 minutes. The specimen is imaged in a BABB bath.

Example 4

Exemplary Tissue Staining Protocol

A specimen is fixed in formalin and 10 µM DAPI using traditional methods or rapid formalin fixation methods, such as with a microwave. The specimen is incubated in methacarn at 40° C. for 60 minutes. The specimen is transferred to a solution of 100% BABB, and incubated for 20 minutes. The specimen is imaged in a BABB bath.

Example 5

Exemplary Tissue Samples Produced Using the Methods of the Invention

FIG. 9 shows various tissue samples, such as an image of an uncleared sample (FIG. 9A) and sample produced with a traditional ethanol/hexane/BABB method of tissue processing (FIG. 9B). This traditional method was used as a comparative example because it is recognized as being significantly faster than alternative clearing methods which typically take days to weeks for adequate clearing. FIG. 9C is an image depicting a sample processed using the methods of the present invention. At time 1.25 hours (15 mins clearing post processing), clearing with the method of the present invention shows deeper clearing (smaller core of uncleared volume) compared to traditional processing. The traditional method also shows leeching of fluorescent dye into BABB (red tint to liquid), indicative of reduced dye binding.

Figure 10:
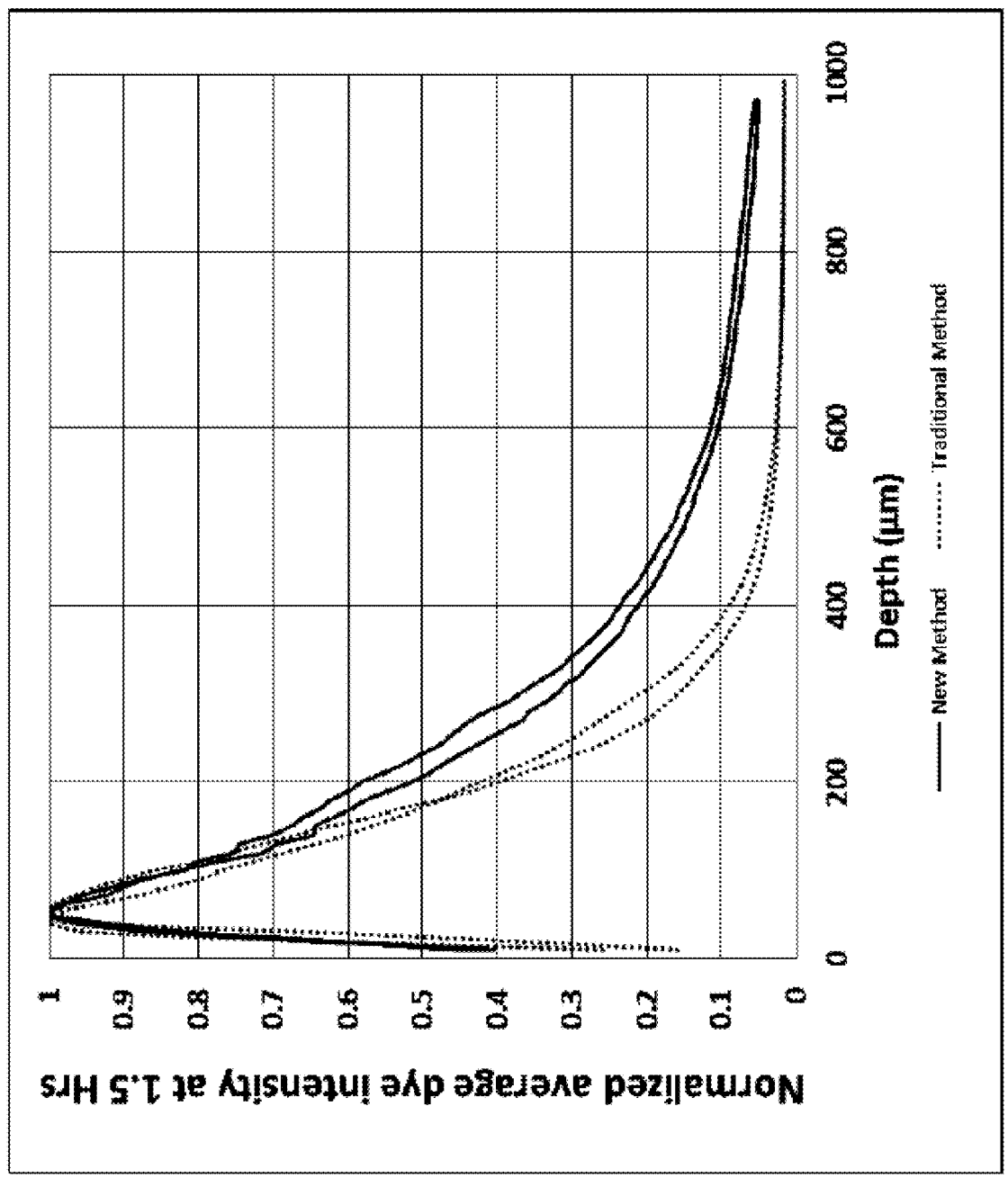
FIG. 10 is a graph depicting the normalized average dye staining with depth at 1.5 h. At time 1.5 h, tissue processing using the methods of the present invention exhibits significantly better dye penetration than ethanol/hexane/BABB traditional processing as described for FIG. 9.

At time 1.5 h, tissue processing using the methods of the present invention exhibits significantly better dye penetration than a fast processing method using standard reagent combinations of increasing ethanol concentrations, followed by hexane, followed by BABB clearing. The normalized average dye staining as a function of depth at 1.5 h is depicted in FIG. 10. These results demonstrate that the use of a permeant during dehydration and dyeing can further increase the rate of sample processing when a dye is incorporated in the dehydration step.

FIG. 11 depicts images of tissues processed using traditional ethanol/hexane/BABB processing methods (FIG. 11A) and using the methods of the present invention (FIG. 11B). The methods of the present invention result in better separation of nuclear and protein fluorescence signals with inexpensive dye combinations (much brighter nuclei in FIG. 11B) and exhibit improved detail at 500 µm deep with significantly less cell shrinkage (smaller average cell size in FIG. 11A) in these images from the same normal human liver. The artifacts created by the traditional process make it unacceptable for clinical interpretation. Also, the images in this figure were obtained after a total processing time of only 1.5 hours, faster than any routine method for clinical tissue slice preparation, including microwave-based methods which are known to adversely affect morphology, and faster than other comparable clearing methods currently in use. In addition, the tissues processed using the methods of the present invention were whole and un-embedded in paraffin, making them available in their entirety for additional testing, which cannot be accomplished using other currently available processing methods.

Figure 12:
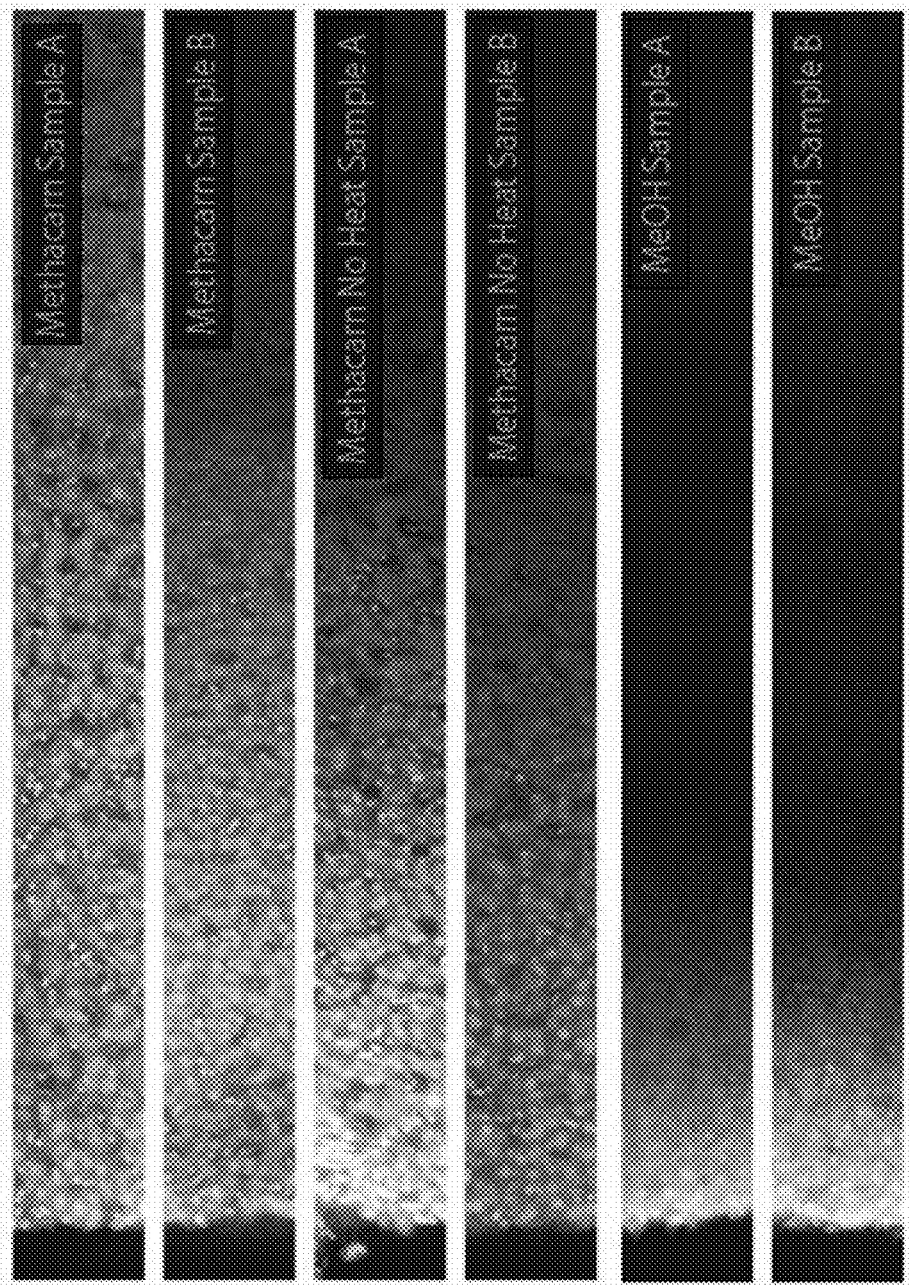
FIG. 12 is a series of images depicting images of tissue samples processed using methacarn or methanol, and treated with heat or without heat.

FIG. 12 is a series of images depicting images of tissue samples processed using methacarn or methanol alone, and treated with heat or without heat.

Figure 13:
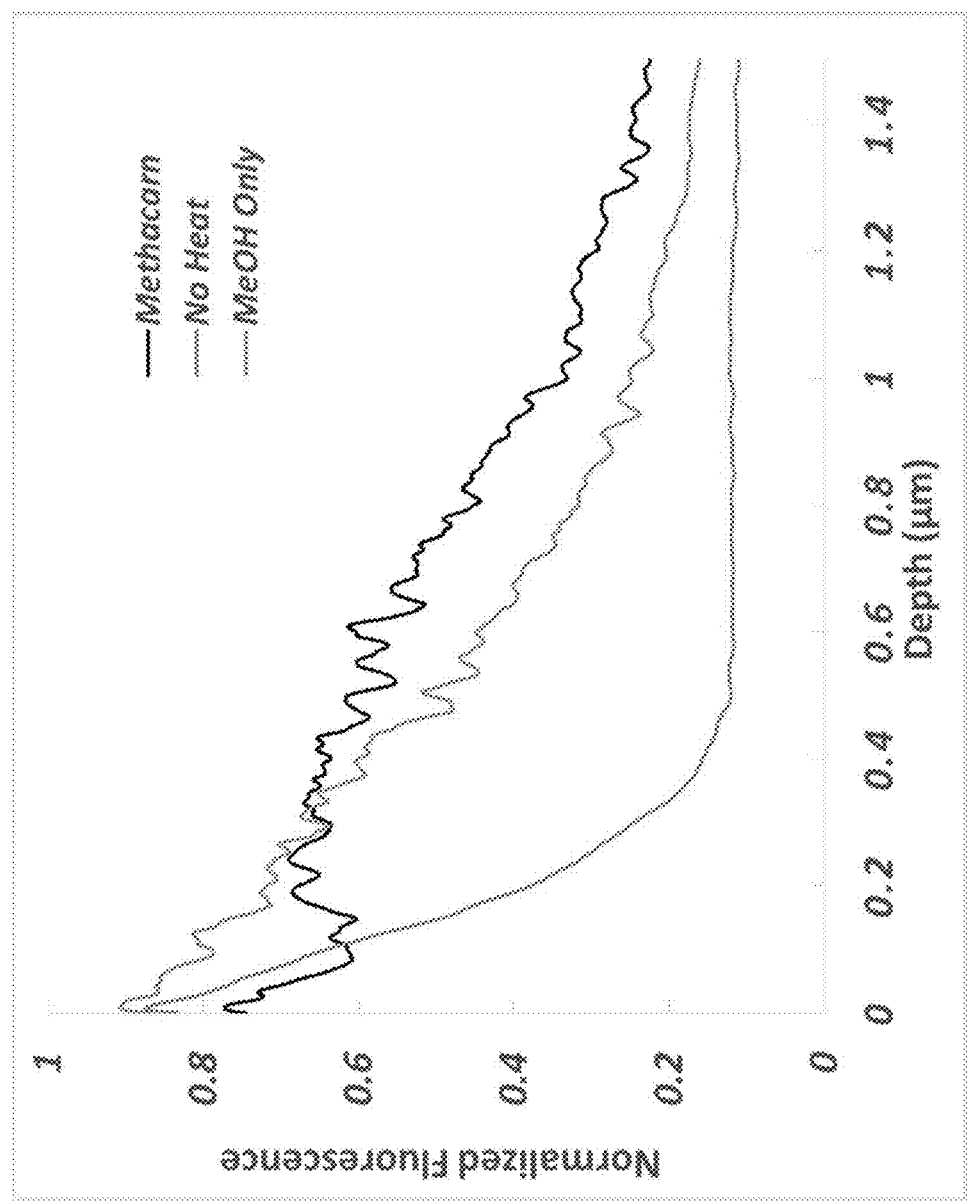
FIG. 13 is a graph depicting normalized staining intensity versus depth for samples processed with methacarn, methanol only, and no heat.

FIG. 13 is a graph derived from the images of FIG. 12 depicting normalized fluorescence staining versus depth for samples processed with methacarn, methanol only, and no heat. This graph demonstrates the benefits of using methacarn, which includes glacial acetic acid as a permeant, and heat for better dye penetration.

FIG. 14 depicts images of tissues processed using pseudo-H&E. FIG. 14A is an image of tissue processed with nuclear stain. FIG. 14B is an image of tissue processed with protein fluorescence. FIG. 14C is an image of tissue imaged with an exponential matrix conversion of fluorescence intensity values using images depicted in FIGS. 14A and 14B. It reproduces near perfectly a traditionally fixed, sectioned, and hematoxylin and eosin stained pathology slide image.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of processing a tissue sample for deep imaging, the method comprising:
    obtaining a tissue sample;
    contacting the tissue sample with a fixative solution at 45° C., the fixative solution comprising methacarn, 10 µM DAPI, and 0.5% by volume eosin for about 1 hour; and
    transferring the tissue sample directly to a solution of 100% benzyl alcohol and benzyl benzoate (BABB) for about 30 minutes.

2. The method of processing a tissue sample for deep imaging according to claim 1, further comprising the step of imaging the tissue sample in the solution of 100% BABB to produce an image of the tissue sample at the depth of 100 nm to 2 cm.

3. The method of processing a tissue sample for deep imaging according to claim 1, wherein the fixative solution further comprises a red blood cell lysing agent.

4. The method of processing a tissue sample for deep imaging according to claim 1, wherein:
the tissue sample obtained is core needle biopsy-sized.

5. The method of processing a tissue sample for deep imaging according to claim 1, wherein the fixative solution comprises:
about 10% of a morphology preservative.

6. The method of processing a tissue sample for deep imaging according to claim 1, further comprising fixing the tissue sample in formalin before contacting the tissue sample with the fixative solution.

7. The method of processing a tissue sample for deep imaging according to claim 6, further comprising fixing the tissue sample in formalin for a period of time from 20 minutes to 4 weeks before contacting the tissue sample with the fixative solution.

* * * * *